United States Patent
Cumming

(10) Patent No.: US 6,846,827 B1
(45) Date of Patent: Jan. 25, 2005

(54) PYRIMIDINE DERIVATIVES

(75) Inventor: John Graham Cumming, Macclesfield Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/070,360

(22) PCT Filed: Oct. 10, 2000

(86) PCT No.: PCT/GB00/03929

§ 371 (c)(1),
(2), (4) Date: Mar. 5, 2002

(87) PCT Pub. No.: WO01/27089

PCT Pub. Date: Apr. 19, 2001

(30) Foreign Application Priority Data

Oct. 13, 1999 (GB) .............................................. 9924092

(51) Int. Cl.[7] .................... C07D 239/42; C07D 239/47; C07D 401/12; A61K 31/506; A61P 19/02
(52) U.S. Cl. .................. 514/256; 514/269; 514/217.06; 514/227.8; 514/231.5; 544/326; 544/328; 544/111; 544/60; 540/598
(58) Field of Search ................................ 544/326, 328; 514/256, 269, 286, 209

(56) References Cited

FOREIGN PATENT DOCUMENTS

| | | |
|---|---|---|
| EP | 0 566 226 A | 10/1993 |
| EP | 0 945 443 A | 9/1999 |
| WO | WO 97/33883 | 9/1997 |
| WO | 98/22103 | 5/1998 |
| WO | WO 99/01439 A | 1/1999 |
| WO | 99/15164 | 4/1999 |
| WO | 99/59959 | 11/1999 |
| WO | 99/59960 | 11/1999 |
| WO | 00/07980 | 2/2000 |
| WO | 00/07991 | 2/2000 |
| WO | 00/12485 | 3/2000 |
| WO | 00/12486 | 3/2000 |
| WO | WO 00/12487 A | 3/2000 |
| WO | 00/18738 | 4/2000 |
| WO | 00/20402 | 4/2000 |
| WO | WO 00/20402 A | 4/2000 |
| WO | 00/55120 | 9/2000 |
| WO | 00/55153 | 9/2000 |
| WO | 00/56738 | 9/2000 |

OTHER PUBLICATIONS

Shaw et al. Expert Opin. Investig. Drugs 9(7) 1469–1478, 2000.*
Brunet et al., Essays Biochem. 32 : 1–16, 1997.*
Nagarkatti et al. J. Mol. Cell Cardiol. 30(8): 1651–1664, 1998.*
Herlaar et al. Mol. Med. Today 5(10) 439–447, 1999.*
Graninger et al., Curr. Opin. Rheumatol. 13(3): 209–213, 2001.*
Hansen, "Review—Pulmonary–Allergy, Dermatological, Gastrointestinal & Arthritis—Inhibitors of p38 kinase", Exp. Opin. Ther. Patents, 1997, XP–002086152, pp. 729–733.

* cited by examiner

Primary Examiner—Venkataraman Balasubramanian
(74) Attorney, Agent, or Firm—Morgan, Lewis & Bockius LLP

(57) ABSTRACT

The invention concerns pyrimidine derivatives of Formula (I) wherein m is 0–3 and each $R^1$ is a group such as hydroxy, halogeno, trifluoromethyl and cyano; $R^3$ is hydrogen, halogeno or (1–6C)alkyl; n is 0–2 and each $R^2$ is a group such as hydroxy, halogeno, trifluoromethyl and cyano; p is 0–4; and $Q^1$ is aryl or heteroaryl; or pharmaceutically acceptable salts or in vivo cleavable esters thereof; processes for their preparation, pharmaceutical compositions containing them and their use in the treatment of diseases or medical conditions mediated by cytokines.

12 Claims, No Drawings

PYRIMIDINE DERIVATIVES

This invention concerns certain novel pyrimidine derivatives and their use as inhibitors of cytokine mediated disease. The invention also concerns processes for the manufacture of said novel pyrimidine derivatives, pharmaceutical compositions containing them and their use in therapeutic methods, for example by virtue of inhibition of cytokine mediated disease.

The pyrimidine derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, adult respiratory distress syndrome and chronic obstructive pulmonary disease), and in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

According to one aspect of the present invention there is provided a pyrimidine derivative of the Formula I

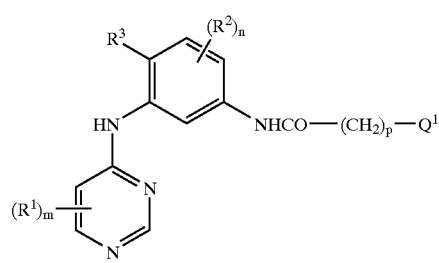

I wherein m is 0, 1, 2 or 3 and each $R^1$ group, which may be the same or different, is selected from hydroxy, halogeno, trifluoromethyl, cyano, mercapto, nitro, amino, carboxy, carbamoyl, formyl, sulphamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl- (2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$Q^2—X^1—$$

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein each $R^4$ is hydrogen or (1–6C)alkyl, and $Q^2$ is aryl-(1–6C)alkyl, heteroaryl-(1–6C)alkyl, heterocyclyl or heterocyclyl-(1–6C)alkyl, or $(R^1)_m$ is (1–3C)alkylenedioxy, and wherein a single pair of adjacent carbon atoms in a (2–6C)alkylene chain within a $R^1$ substituent is optionally separated by the insertion of a group selected from O, S, SO, $SO_2$, $N(R^5)$, CO, $CH(OR^5)$, $CON(R^5)$, $N(R^5)CO$, $SO_2N(R^5)$ and $N(R^5)SO_2$ wherein $R^5$ is hydrogen or (1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl(1–6C)alkanesulphonylamino, or from a group of the formula:

$$—X^2—Q^3$$

wherein $X^2$ is a direct bond or is selected from O and $N(R^7)$, wherein $R^7$ is hydrogen or (1–6C)alkyl, and $Q^3$ is aryl, aryl-(1–6C)alkyl, heteroaryl, heteroaryl-(1–6C)alkyl, heterocyclyl or heterocyclyl-(1–6C)alkyl, and any $Q^3$ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl]amino, and wherein any heterocyclyl group within a substituent on $R^1$ optionally bears 1 or 2 oxo or thioxo substituents, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkyl carbamoyl, N,N-di-[(1–6C)alkyl]carbamoyl, (2–6C)alkanoyl, (2–6C)alkanoyloxy, (2–6C)alkanoylamino, N-(1–6C)alkyl(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino;

$R^3$ is hydrogen, halogeno or (1–6C)alkyl;

n is 0, 1 or 2 and each $R^2$ group, which may be the same or different, is selected from hydroxy, halogeno, trifluoromethyl, cyano, mercapto, nitro, amino, carboxy, (1–6C)alkoxycarbonyl, (1–6C)alkyl, (1–6C)alkoxy, (1–6C)alkylamino and di-[(1–6C)alkyl]amino;

p is 0, 1, 2, 3 or 4; and $Q^1$ is aryl or heteroaryl and $Q^1$ is optionally substituted with 1, 2 or 3 substituents, which may be the same or different, selected from hydroxy, halogeno, trifluoromethyl, cyano, mercapto, nitro, amino, carboxy, carbamoyl, formyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino or with a (1–3C)alkylenedioxy group, or from a group of the formula:

$$—X^3—Q^4$$

wherein $X^3$ is a direct bond or is selected from O and $N(R^8)$, wherein $R^8$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and any $Q^4$ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl]amino, and wherein any heterocyclyl group within a substituent on $Q^1$ optionally bears 1 or 2 oxo or thioxo substituents, and wherein a single pair of adjacent carbon atoms in a (2–6C)alkylene chain within a $Q^1$ substituent is optionally separated by the insertion of a group selected from O, S, SO, $SO_2$, $N(R^9)$, CO, $CH(OR^9)$, $CON(R^9)$, $N(R^9)CO$, $SO_2N(R^9)$ and $N(R^9)SO_2$ wherein $R^9$ is hydrogen or (1–6C)alkyl, and wherein any $CH_2$ or $CH_3$ group within a $Q^1$ group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino;

or a pharmaceutically-acceptable salt or in-vivo-cleavable ester thereof.

In this specification, the term (1–6C)alkyl includes straight and branched chain alkyl groups such as propyl, isopropyl and tert-butyl, unsaturated alkyl groups, for example (2–6C)alkenyl groups such as vinyl and allyl and (2–6C)alkynyl groups such as ethynyl and propargyl, (3–6C)cycloalkyl groups such as cyclopropyl, cyclobutyl, cyclopentyl and cyclohexyl and (3–6C)cycloalkenyl groups such as cyclopentenyl and cyclohexenyl. References to individual alkyl groups such as propyl are specific for the straight chain version only and references to individual branched chain alkyl groups such as isopropyl are specific for the branched chain version only. A similar convention applies to other generic groups, for example (1–6C)alkoxy includes methoxy, ethoxy, vinyloxy, allyloxy, propargyloxy, cyclopropyloxy and cyclopentyloxy, (1–6C)alkylamino includes methylamino, ethylamino, allylamino, propargylamino, cyclobutylamino and cyclohexylamino, di-

[(1–6Calkyl]amino includes dimethylamino, diethylamino, N-allyl-N-methylamino, N-methyl-N-propargylamino, N-cyclobutyl-N-methylamino and N-cyclohexyl-N-ethylamino and (2–6C)alkanoylamino includes acetamido, propionamido, acrylamido and propiolamido.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is further to be understood that, insofar as certain of the pyrimidine derivatives of Formula I defined above may exhibit the phenomenon of tautomerism, for example by virtue of one or more hydroxy, mercapto or amino substituents on the pyrimidine ring, the invention includes in its definition any tautomeric form which possesses the above-mentioned activity. In particular, the invention is not to be limited merely to any one tautomeric form utilised within the formulae drawings or within any Table within the Examples which are set out hereinafter.

Suitable values for the generic radicals referred to above include those set out below.

A suitable value for any one of the 'Q' groups ($Q^1$ to $Q^4$) when it is aryl or for the aryl group within a 'Q' group is, for example, phenyl, naphthyl, indenyl, indanyl, tetrahydronaphthyl or fluorenyl, preferably phenyl.

A suitable value for any one of the 'Q' groups ($Q^1$ to $Q^4$) when it is heteroaryl or for the heteroaryl group within a 'Q' group is, for example, an aromatic 5- or 6-membered monocyclic ring, a 9- or 10-membered bicyclic ring or a 13- or 14-membered tricyclic ring each containing 1 oxygen heteroatom or 1 or 2 nitrogen heteroatoms and optionally containing a further heteroatom selected from nitrogen, oxygen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl, pyridyl, benzothiophenyl, benzofurazanyl, quinolyl, carbazolyl, dibenzofuranyl or dibenzothiophenyl, even more preferably pyridyl.

A suitable value for any one of the 'Q' groups ($Q^1$ to $Q^4$) when it is heterocyclyl or for the heterocyclyl group within a 'Q' group is, for example, a non-aromatic saturated or partially saturated 3- to 10-membered monocyclic or bicyclic ring with up to three heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, imidazolinyl, imidazolidinyl, pyrazolinyl, pyrazolidinyl, 1,1-dioxidoisothiazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl or benzo derivatives thereof such as 2,3-dihydrobeenzofuranyl, 2,3-dihydrobenzothienyl, indolinyl, isoindolinyl, chromanyl and isochromanyl, preferably azetidin-1-yl, 3-pyrrolin-1-yl, pyrrolidin-1-yl, pyrrolidin-2-yl, pyrrolidin-3-yl, morpholino, 1,1-dioxotetrahydro-4H-1,4-thiazin-4-yl, piperidino, piperidin-3-yl, piperidin-4-yl, homopiperidin-1-yl, piperazin-1-yl, piperazin-2-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl or heterocyclyl-(1–6C)alkyl group is present.

Suitable values for any of the 'R' groups ($R^1$ to $R^9$), or for various groups within an $R^1$ substituent, or within a substituent on $Q^1$ include:—

| | |
|---|---|
| for halogeno | fluoro, chloro, bromo and iodo; |
| for (1-6C)alkyl: | methyl, ethyl, vinyl, ethynyl, propyl, allyl, propargyl, isopropyl, cyclopropyl, tert-butyl, cyclobutyl, cyclopentyl, cyclopentenyl, cyclohexyl and cyclohexenyl; |
| for (1-6C)alkoxy: | methoxy, ethoxy, vinyloxy, propoxy, allyloxy, isopropoxy, propargyloxy, cyclopropyloxy, butoxy and cyclopentyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, allylamino, propargylamino, isopropylamino, butylamino, cyclobutylamino and cyclohexylamino; |
| for di-[(1-6C)alkyl]amino: | dimethylamino, diethylamino, N-ethyl-N-methylamino, diisopropylamino, N-allyl-N-methylamino, N-methyl-N-propargylamino, N-cyclobutyl-N-methylamino and N-cyclohexyl-N-ethylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido, propionamido, acrylamido, methacrylamido, crotonamido and propiolamido; |
| for N-(1-6C)alkyl-(2-6C)alkanoylamino: | N-methylacetamido, N-methylpropionamido, N-methylacrylamido and N-methylpropiolamido; |
| for N-(1-6C)alkylsulphamoyl: | N-methylsulphamoyl and N-ethylsulphamoyl; |

| | |
|---|---|
| -continued | |
| for N,N-di-[(1-6C)alkyl] sulphamoyl: | N,N-dimethylsulphamoyl; |
| for (1-6C)alkanesulphonyl- amino: | methanesulphonylamino, ethanesulphonylamino, vinylsulphonylamino and ethynylsulphonylamino; |
| for N-(1-6C)alkyl-(1-6C) alkanesulphonylamino: | N-methylmethanesulphonylamino, N-methylethanesulphonylamino, N-methylvinylsulphonylamino and N-methylethynylsulphonylamino. |

A suitable value for $(R^1)_m$ or for a substituent on $Q^1$ when it is (1–3C)alkylenedioxy is, for example, methylenedioxy or ethylenedioxy and the oxygen atoms thereof occupy adjacent ring positions.

When, as defined hereinbefore, an $R^1$ group forms a group of the formula $Q^2—X^1—$ and, for example, $X^1$ is a $OC(R^4)_2$ linking group, it is the carbon atom, not the oxygen atom, of the $OC(R^4)_2$ linking group which is attached to the pyrimidine ring of Formula I and the oxygen atom is attached to the $Q^2$ group. A similar convention applies to the attachment of other groups of the formula $Q^2—X^1—$.

As defined hereinbefore, a single pair of adjacent carbon atoms in a (2–6C)alkylene chain within a $R^1$ substituent is optionally separated by the insertion of a group such as O or $CON(R^5)$ and a single pair of adjacent carbon atoms in a (2–6C)alkylene chain within a $Q^1$ substituent is optionally separated by the insertion of a group such as O or $CON(R^9)$. For example, insertion of a CONH group into the propylene chain within a 3-methoxypropoxy group gives rise to, for example, a 2-(2-methoxyacetamido)ethoxy group.

When, as defined hereinbefore, any $CH_2$ or $CH_3$ group within a $R^1$ substituent optionally bears oh each said $CH_2$ or $CH_3$ group one or more halogeno substituents, there are suitably 1 or 2 halogeno substituents present on each said $CH_2$ group and there are suitably 1, 2 or 3 halogeno substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, amino-substituted (2–6C)alkoxy groups such as 3-aminopropoxy, (1–6C)alkylamino-substituted (2–6C)alkoxy groups such as 3-methylaminopropoxy, di-[(1–6C)alkyl]amino-substituted (2–6C)alkoxy groups such as 2-dimethylaminopropoxy, 3-dimethylaminopropoxy and 3-dimethylamino-2,2-dimethylpropoxy, amino-substituted (2–6C)alkylamino groups such as 3-aminopropylamino, (1–6C)alkylamino-substituted (2–6C)alkylamino groups such as 3-methylaminopropylamino, di-[(1–6C)alkyl]amino-substituted (2–6C)alkylamino groups such as 2-dimethylaminopropylamino, 3-dimethylaminopropyl-amino and 3-dimethylamino-2,2-dimethylpropylamino, hydroxy-substituted heterocyclyl-(1–6C)alkoxy groups such as 2-hydroxy-3-piperidinopropoxy and 2-hydroxy-3-morpholinopropoxy, hydroxy-substituted amino-(2–6C) alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C) alkylamino-(2–6C)alkylamino groups such as 2-hydroxy-3-methylaminopropylamino, hydroxy-substituted di-[(1–6C) alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy and (1–6C) alkylsulphonyl-substituted (1–6C)alkoxy groups such as 2-methylsulphonylethoxy.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, *Advanced Drug Delivery Reviews*, 8, 1–38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1–6C)alkoxymethyl esters, for example methoxymethyl; (1–6C)alkanoyloxymethyl esters, for example pivaloyloxymethyl; phthalidyl esters; (3–8C)cycloalkoxycarbonyloxy(1–6C)alkyl esters, for example 1-cyclohexylcarbonyloxyethyl; 1,3-dioxolan-2-ylmethyl esters, for example 5-methyl-1,3-dioxolan-2-ylmethyl; and (1–6C)alkoxycarbonyloxyethyl esters, for example 1-methoxycarbonyloxyethyl; and may be formed at any carboxy group in the compounds of this invention.

Particular novel compounds of the invention include, for example, pyrimidine derivatives of the Formula I, or pharmaceutically-acceptable salts thereof, wherein, unless otherwise stated, each of m, $R^1$, n, $R^2$, $R^3$, p and $Q^1$ has any of the meanings defined hereinbefore or in relevant paragraphs selected from paragraphs (a) to (u) hereinafter:—

(a) m is 0, 1, 2 or 3, and each $R^1$ group, which may be the same or different, is selected from hydroxy, halogeno, trifluoromethyl, amino, carbamoyl, (1–6C)alkyl, (1–6C) alkoxy, (1–6C)alkylthio, (1–6C)alkylsulphinyl, (1–6C) alkylsulphonyl, (1–6C)alkylamino, di-[(1–6C)alkyl] amino, N-(1–6C)alkylcarbamoyl, N,N-di-[(1–6C)alkyl] carbamoyl, (2–6C)alkanoyl amino and N-(1–6C)alkyl-(2–6C)alkanoylamino,
or from a group of the formula:

$$Q^2—X^1—$$

wherein $X^1$ is a direct bond or is selected from O, $N(R^4)$, $CON(R^4)$, $N(R^4)CO$ and $OC(R^4)_2$ wherein $R^4$ is hydrogen or (1–6C)alkyl, and $Q^2$ is aryl-(1–6C)alkyl, heteroaryl-(1–6C)alkyl, heterocyclyl or heterocyclyl-(1–6C)alkyl, and wherein a single pair of adjacent carbon atoms in a (2–6C)alkylene chain within a $R^1$ substituent is optionally separated by the insertion of a group selected from O, $N(R^5)$, $CON(R^5)$ and $N(R^5)CO$ wherein $R^5$ is hydrogen or (1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carboxy, (1–6C)alkyl, (1–6C)alkoxy and (1–6C)alkoxycarbonyl, and wherein any heterocyclyl group within a substituent on $R^1$ optionally bears 1 or 2 oxo substituents, and wherein any $CH_2$ or $CH_3$ group within a $R^1$ substituent optionally bears on each said $CH_2$ or $CH_3$ group one or more (1–6C)alkyl substituents or a substituent selected from hydroxy, amino, (1–6C)alkoxy, (1–6C)alkylsulphonyl, (1–6C)alkylamino and di-[(1–6C)alkyl]amino;

(b) m is 0, 1, 2 or 3, and each $R^1$ group, which may be the same or different, is selected from hydroxy, fluoro, chloro, bromo, trifluoromethyl, amino, carbamoyl, methyl, ethyl, propyl, vinyl, ethynyl, methoxy, ethoxy, propoxy, methylthio, ethylthio, methylsulphinyl, methylsulphonyl, methylamino, ethylamino, propylamino, isopropylamino, butylamino, allylamino, propargylamino, dimethylamino, diethylamino, dipropylamino, N-allyl-N-methylamino, N-methylcarbamoyl, N,N-dimethylcarbamoyl, acetamido, propionamido, acrylamido and propiolamido, or from a group of the formula:

$Q^2-X^1-$ wherein $X^1$ is a direct bond or is selected from O, NH, N(Me), CONH, NHCO and $OCH_2$ and $Q^2$ is benzyl, furylmethyl, thienylmethyl, imidazolylmethyl, 2-imidazolylethyl, 3-imidazolylpropyl, 4-imidazolylbutyl, oxazolylmethyl, thiazolylmethyl, 1,2,3-triazolylmethyl, 2-(1,2,3-triazolyl)ethyl, 3-(1,2,3-triazolyl)propyl, 1,2,4-triazolylmethyl, 2-(1,2,4-triazolyl)ethyl, 3-(1,2,4-triazolyl)propyl, pyridylmethyl, 2-pyridylethyl, 3-pyridylpropyl, pyrrolidinyl, morpholinyl, tetrahydro-4H-1,4-thiazinyl, 1,1-dioxotetrahydro-4H-1,4-thiazinyl, piperidinyl, homopiperidinyl, piperazinyl, homopiperazinyl, pyrrolidinylmethyl, 2-pyrrolidinylethyl, 3-pyrrolidinylpropyl, imidazolidinylmethyl, 2-imidazolidinylethyl, 3-imidazolidinylpropyl, morpholinylmethyl, 2-morpholinylethyl, 3-morpholinylpropyl, tetrahydro-4H-1,4-thiazinylmethyl, 1,1-dioxotetrahydro-4H-1,4-thiazinylmethyl, 2-(tetrahydro-4H-1,4-thiazinyl)ethyl, 2-(1,1-dioxotetrahydro-4H-1,4-thiazinyl)ethyl, 3-(tetrahydro-4H-1,4-thiazinyl)propyl, 3-(1,1-dioxotetrahydro-4H-1,4-thiazinyl)propyl, piperidinylmethyl, 2-piperidinylethyl, 3-piperidinylpropyl, homopiperidinylmethyl, 2-homopiperidinylethyl, 3-homopiperidinylpropyl, piperazinylmethyl, 2-piperazinylethyl, 3-piperazinylpropyl, homopiperazinylmethyl, 2-homopiperazinylethyl or 3-homopiperazinylpropyl, and wherein a single pair of adjacent carbon atoms in a (2–6C)alkylene chain within a $R^1$ substituent is optionally separated by the insertion of a group selected from O, NH, CONH and NHCO, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy, propoxy, isopropoxy, methoxycarbonyl, ethoxycarbonyl and tert-butoxycarbonyl, and wherein any heterocyclyl group within a substituent on $R^1$ optionally bears 1 or 2 oxo substituents, and wherein any $CH_2$ or $CH_3$ group within a $R^1$ substituent optionally bears on each said $CH_2$ or $CH_3$ group 1 or 2 methyl substituents or a substituent selected from hydroxy, amino, methoxy, ethoxy, methylsulphonyl, methylamino, ethylamino, dimethylamino and diethylamino;

(c) m is 0, 1, 2 or 3, and each $R^1$ group, which may be the same or different, is selected from hydroxy, fluoro, chloro, bromo, trifluoromethyl, amino, carbamoyl, methyl, ethyl, propyl, methoxy, ethoxy, propoxy, methylthio, methylsulphinyl, methylsulphonyl, methylamino, ethylamino, propylamino, isopropylamino, butylamino, allylamino, propargylamino, dimethylamino, diethylamino, dipropylamino, N-allyl-N-methylamino; N-methylcarbamoyl, N,N-dimethylcarbamoyl and acetamido, or from a group of the formula:

$Q^2-X^1-$ wherein $X^1$ is a direct bond or is selected from O, NH, N(Me), CONH, NHCO and $OCH_2$ and $Q^2$ is benzyl, 2-furylmethyl, 3-furylmethyl, 2-thienylmethyl, 3-thienylmethyl, 1-imidazolylmethyl, 2-imidazolylmethyl, 2-imidazol-1-ylethyl, 3-imidazol-1-ylpropyl, 4-imidazol-1-ylbutyl, 2-oxazolylmethyl, 4-oxazolylmethyl, 5-oxazolylmethyl, 2-thiazolylmethyl, 4-thiazolylmethyl, 5-thiazolylmethyl, 1,2,3-triazol-1-ylmethyl, 2-(1,2,3-triazol-1-yl)ethyl, 3-(1,2,3-triazol-1-yl)propyl, 1,2,4-triazol-1-ylmethyl, 2-(1,2,4-triazol-1-yl)ethyl, 3-(1,2,4-triazol-1-yl)propyl, 2-pyridylmethyl, 3-pyridylmethyl, 4-pyridylmethyl, 2-pyrid-2-ylethyl, 2-pyrid-3-ylethyl, 2-pyrid-4-ylethyl, 3-pyrid-2-ylpropyl, 3-pyrid-3-ylpropyl, 3-pyrid-4-ylpropyl, pyrrolidin-1-yl, pyrrolidin-2-yl, pyrrolidin-3-yl, morpholino, tetrahydro-4H-1,4-thiazin-4-yl, 1,1-dioxotetrahydro-4H-1,4-thiazin-4-yl, piperidino, piperidin-2-yl, piperidin-3-yl, piperidin-4-yl, homopiperidin-1-yl, homopiperidin-2-yl, homopiperidin-3-yl, homopiperidin-4-yl, piperazin-1-yl, homopiperazin-1-yl, pyrrolidin-1-ylmethyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, pyrrolidin-3-ylmethyl, 2-pyrrolidin-3-ylethyl, 3-pyrrolidin-3-ylpropyl, imidazolidin-1-ylmethyl, 2-imidazolidin-1-ylethyl, 3-imidazolidin-1-ylpropyl, imidazolidin-2-ylmethyl, 2-imidazolidin-2-ylethyl, 3-imidazolidin-2-ylpropyl, morpholinomethyl, 2-morpholinoethyl, 3-morpholinopropyl, morpholin-2-ylmethyl, 2-morpholin-2-ylethyl, 3-morpholin-2-ylpropyl, morpholin-3-ylmethyl, 2-morpholin-3-ylethyl, 3-morpholin-3-ylpropyl, tetrahydro-4H-1,4-thiazin-4-ylmethyl, 2-(tetrahydro-4H-1,4-thiazin-4-yl)ethyl, 3-(tetrahydro-4H-1,4-thiazin-4-yl)propyl, 1,1-dioxotetrahydro-4H-1,4-thiazin-4-ylmethyl, 2-(1,1-dioxotetrahydro-4H-1,4-thiazin-4-yl)ethyl, 3-(1,1-dioxotetrahydro-4H-1,4-thiazin-4-yl)propyl, piperidinomethyl, 2-piperidinoethyl, 3-piperidinopropyl, piperidin-2-ylmethyl, 2-piperidin-2-ylethyl, 3-piperidin-2-ylpropyl, piperidin-3-ylmethyl, 2-piperidin-3-ylethyl, 3-piperidin-3-ylpropyl, piperidin-4-ylmethyl, 2-piperidin-4-ylethyl, 3-piperidin-4-ylpropyl, homopiperidin-1-ylmethyl, 2-homopiperidin-1-ylethyl, 3-homopiperidin-1-ylpropyl, homopiperidin-2-ylmethyl, 2-homopiperidin-2-ylethyl, 3-homopiperidin-2-ylpropyl, homopiperidin-3-ylmethyl, 2-homopiperidin-3-ylethyl, 3-homopiperidin-3-ylpropyl, homopiperidin-4-ylmethyl, 2-homopiperidin-4-ylethyl, 3-homopiperidin-4-ylpropyl, piperazin-1-ylmethyl, 2-piperazin-1-ylethyl, 3-piperazin-1-ylpropyl, piperazin-2-ylmethyl, 2-piperazin-2-ylethyl, 3-piperazin-2-ylpropyl, homopiperazin-1-ylmethyl, 2-homopiperazin-1-ylethyl, 3-homopiperazin-1-ylpropyl, homopiperazin-2-ylmethyl, 2-homopiperazin-2-ylethyl or 3-homopiperazin-2-ylpropyl, and wherein a single pair of adjacent carbon atoms in a (2–6C)alkylene chain within a $R^1$ substituent is optionally separated by the insertion of a group selected from O, NH, CONH and NHCO, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy, propoxy, isopropoxy, methoxycarbonyl, ethoxycarbonyl and tert-butoxycarbonyl, and wherein any heterocyclyl group within a substituent on $R^1$ optionally bears 1 or 2 oxo substituents;

and wherein any $CH_2$ or $CH_3$ group within a $R^1$ substituent optionally bears on each said $CH_2$ or $CH_3$ group 1 or 2 methyl substituents or a substituent selected from hydroxy, amino, methoxy, ethoxy, methylsulphonyl, methylamino, ethylamino, dimethylamino and diethylamino;

(d) m is 0, 1 or 2 and each $R^1$ group, which may be the same or different, is selected from hydroxy, fluoro, chloro, bromo, trifluoromethyl, amino, carbamoyl, methyl, ethyl, propyl, methoxy, ethoxy, propoxy, methylthio, methylamino, ethylamino, propylamino, isopropylamino, butylamino, allylamino, propargylamino, dimethylamino, diethylamino, dipropylamino, N-allyl-N-methylamino, N-methylcarbamoyl, N,N-dimethylcarbamoyl, acetamido, benzyl, benzyloxy, benzylamino, N-benzyl-N-methylamino, 2-furylmethoxy, 3-furylmethoxy, 2-thienylmethoxy, 3-thienylmethoxy, 1-imidazolylmethoxy, 2-imidazolylmethoxy, 2-imidazol-1-ylethoxy, 3-imidazol-1-ylpropoxy, 2-imidazol-1-ylethylamino, 3-imidazol-1-ylpropylamino, 2-oxazolylmethoxy, 4-oxazolylmethoxy, 5-oxazolylmethoxy, 2-thiazolylmethoxy, 4-thiazolylmethoxy, 5-thiazolylmethoxy, 1,2,3-triazol-1-ylmethoxy, 2-(1,2,3-triazol-1-yl)ethoxy, 3-(1,2,3-triazol-1-yl)propoxy, 1,2,3-triazol-1-ylmethylamino, 2-(1,2,3-triazol-1-yl)ethylamino, 3-(1,2,3-triazol-1-yl) propylamino, 1,2,4-triazol-1-ylmethoxy, 2-(1,2,4-triazol-1-yl)ethoxy, 3-(1,2,4-triazol-1-yl)propoxy, 1,2,4-triazol-1-ylmethylamino, 2-(1,2,4-triazol-1-yl)ethylamino, 3-(1,2,4-triazol-1-yl)propylamino, 2-pyridylmethoxy, 3-pyridylmethoxy, 4-pyridylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, pyrrolidin-3-yloxy, pyrrolidin-3-ylamino, N-methyl-N-(3-pyrrolidinyl) amino, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethoxy, 3-imidazolidin-1-ylpropoxy, imidazolidin-2-ylmethoxy, 2-imidazolidin-2-ylethoxy, 3-imidazolidin-2-ylpropoxy, 2-imidazolidin-1-ylethylamino, 3-imidazolidin-1-ylpropylamino, 2-imidazolidin-2-ylethylamino, 3-imidazolidin-2-ylpropylamino, 2-morpholinoethoxy, 3-morpholinopropoxy, 2-morpholinoethylamino, 3-morpholinopropylamino, morpholin-2-ylmethoxy, 2-morpholin-2-ylethoxy, 3-morpholin-2-ylpropoxy, 2-morpholin-2-ylethylamino, 3-morpholin-2-ylpropylamino, morpholin-3-ylmethoxy, 2-morpholin-3-ylethoxy, 3-morpholin-3-ylpropoxy, 2-morpholin-3-ylethylamino, 3-morpholin-3-ylpropylamino, 2-(tetrahydro-4H-1,4-thiazin-4-yl)ethoxy, 3-(tetrahydro-4H-1,4-thiazin-4-yl)propoxy, 2-(tetrahydro-4H-1,4-thiazin-4-yl)ethylamino, 3-(tetrahydro-4H-1,4-thiazin-4-yl)propylamino, 2-(1,1-dioxotetrahydro-4H-1,4-thiazin-4-yl)ethoxy, 3-(1,1-dioxotetrahydro-4H-1,4-thiazin-4-yl)propoxy, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethoxy, 3-piperidinopropoxy, 2-piperidinoethylamino, 3-piperidinopropylamino, piperidin-2-ylmethoxy, 2-piperidin-2-ylethoxy, 3-piperidin-2-ylpropoxy, piperidin-2-ylmethylamino, 2-piperidin-2-ylethylamino, 3-piperidin-2-ylpropylamino, piperidin-3-ylmethoxy, 2-piperidin-3-ylethoxy, 3-piperidin-3-ylpropoxy, piperidin-3-ylmethylamino, 2-piperidin-3-ylethylamino, 3-piperidin-3-ylpropylamino, piperidin-4-ylmethoxy, 2-piperidin-4-ylethoxy, 3-piperidin-4-ylpropoxy, piperidin-4-ylmethylamino, 2-piperidin-4-ylethylamino, 3-piperidin-4-ylpropylamino, 2-homopiperidin-1-ylethoxy, 3-homopiperidin-1-ylpropoxy, 2-homopiperidin-1-ylethylamino, 3-homopiperidin-1-ylpropylamino, homopiperidin-2-ylmethoxy, homopiperidin-2-ylmethylamino, homopiperidin-3-ylmethoxy, homopiperidin-3-ylmethylamino, homopiperidin-4-ylmethoxy, homopiperidin-4-ylmethylamino, 2-piperazin-1-ylethoxy, 3-piperazin-1-ylpropoxy, 2-piperazin-1-ylethylamino, 3-piperazin-1-ylpropylamino, piperazin-2-ylmethoxy, piperazin-2-ylmethylamino, 2-piperazin-2-ylethoxy, 3-piperazin-2-ylpropoxy, 2-piperazin-2-ylethylamino, 3-piperazin-2-ylpropylamino, 2-homopiperazin-1-ylethoxy, 3-homopiperazin-1-ylpropoxy, 2-homopiperazin-1-ylethylamino, 3-homopiperazin-1-ylpropylamino, homopiperazin-2-ylmethoxy and homopiperazin-2-ylmethylamino, and wherein a single pair of adjacent carbon atoms in a (2–6C)alkylene chain within a $R^1$ substituent is optionally separated by the insertion of an O or NH group, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy, propoxy, isopropoxy, methoxycarbonyl, ethoxycarbonyl and tert-butoxycarbonyl, and wherein any heterocyclyl group within a substituent on $R^1$ optionally bears 1 or 2 oxo substituents, and wherein any CH₂ or CH₃ group within a R¹ substituent optionally bears on each said CH₂ or CH₃ group 1 or 2 methyl substituents or a substituent selected from hydroxy, amino, methoxy, ethoxy, methylsulphonyl, methylamino, ethylamino, dimethylamino and diethylamino;

(e) n is 0;
(f) R³ is (1–6C)alkyl;
(g) R³ is methyl;
(h) p is 0;
(i) Q¹ is aryl or heteroaryl and Q¹ is optionally substituted with 1, 2 or 3 substituents, which may be the same or different, selected from hydroxy, halogeno, trifluoromethyl, cyano, amino, (1–6C)alkyl, (1–6C)alkoxy, (1–6C)alkylamino, di-[(1–6C)alkyl]amino, (2–6C)alkanoyloxy, (2–6C)alkanoylamino, N-(1–6C)alkyl-(2–6C)alkanoylamino, (1–6C)alkanesulphonylamino and N-(1–6C)alkyl-(1–6C)alkanesulphonylamino, or from a group of the formula:

wherein X³ is a direct bond or is selected from O, NH and N(Me) and Q⁴ is aryl, heteroaryl or heterocyclyl, and any Q⁴ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl]amino, and wherein any Q⁴ group when it is heterocyclyl optionally bears 1 or 2 oxo substituents, and wherein any CH₂ or CH₃ group within a Q¹ group optionally bears on each said CH₂ or CH₃ group one or more (1–6C)alkyl substituents or a substituent selected from hydroxy, amino, (1–6C)alkoxy, (1–6C) alkylamino and di-[(1–6C)alkyl]amino;

(j) Q¹ is a phenyl group or a heteroaryl group comprising an aromatic 5- or 6-membered monocyclic ring, a 9- or 10-membered bicyclic ring or a 13- or 14-membered tricyclic ring each containing 1 oxygen heteroatom or 1 or 2 nitrogen heteroatoms and optionally containing a further heteroatom selected from nitrogen, oxygen and sulphur, and Q¹ is optionally substituted with 1, 2 or 3 substituents, which may be the same or different, selected from hydroxy, halogeno, trifluoromethyl, cyano, amino, (1–6C) alkyl, (1–6C)alkoxy, (1–6C)alkylamino, di-[(1–6C)alkyl] amino, (2–6C)alkanoyloxy, (2–6C)alkanoylamino, N-(1–6C)alkyl-(2–6C)alkanoylamino, (1–6C) alkanesulphonylamino and N-(1–6C)alkyl-(1–6C) alkanesulphonylamino, or from a group of the formula:

wherein X³ is a direct bond or is selected from O, NH and N(Me) and Q⁴ is phenyl, a heteroaryl group comprising an aromatic 5- or 6-membered monocyclic ring containing 1 oxygen heteroatom or 1 or 2 nitrogen heteroatoms and optionally containing a further heteroatom selected from nitrogen, oxygen and sulphur or a heterocyclyl group comprising a non-aromatic saturated or partially saturated 3- to 10-membered monocyclic ring with up to 3 heteroatoms selected from oxygen, nitrogen and sulphur, and any Q⁴ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl] amino, and wherein any Q⁴ group when it is a heterocyclyl group optionally bears 1 or 2 oxo substituents, and wherein any CH₂ or CH₃ group within a Q¹ group optionally bears on each said CH₂ or CH₃ group one or more (1–6C)alkyl substituents or a substituent selected from hydroxy, amino, (1–6C)alkoxy, (1–6C) alkylamino and di-[(1–6C)alkyl]amino;

(k) Q¹ is optionally substituted with 1, 2 or 3 substituents, which may be the same or different, selected from hydroxy, fluoro, chloro, bromo, trifluoromethyl, cyano, amino, methyl, ethyl, propyl, vinyl, ethynyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetoxy, acetamido, propionamido, acrylamido, propiolamido, N-methylacetamido, methanesulphonylamino, ethanesulphonylamino and N-methylmethanesulphonylamino, or from a group of the formula:

wherein X³ is a direct bond or is selected from O, NH and N(Me) and Q⁴ is phenyl, furyl, thienyl, imidazolyl, oxazolyl, thiazolyl, pyridyl, pyridazinyl, pyrimidinyl, pyrazinyl, azetidinyl, tetrahydrofuranyl, pyrrolinyl, pyrrolidinyl, morpholinyl, tetrahydro-4H-1,4-thiazinyl, 1,1-dioxotetrahydro-4H-1,4-thiazinyl, piperidinyl, homopiperidinyl, piperazinyl or homopiperazinyl, and any Q⁴ group optionally bears 1 or 2 substituents, which may be the same or different, selected from fluoro, chloro, bromo, trifluoromethyl, hydroxy, amino, methyl, ethyl, propyl, vinyl, ethynyl, methoxy, ethoxy, propoxy, methylamino, ethylamino, propylamino, isopropylamino, dimethylamino and diethylamino, and wherein any Q⁴ group when it is a heterocyclyl group optionally bears 1 or 2 oxo substituents, and wherein any CH₂ or CH₃ group within a Q¹ group optionally bears on each said CH₂ or CH₃ group 1 or 2 methyl substituents or a substituent selected from hydroxy, amino, methoxy, ethoxy, propoxy, methylamino, ethylamino, propylamino, isopropylamino, dimethylamino and diethylamino;

(l) Q¹ is optionally substituted with 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonyl-amino, 1-azetidinyl, 2- or 3-tetrahydrofuranyl, 3-pyrrolin-1-yl, 1-pyrrolidinyl, morpholino, tetrahydro-4H-1,4-thiazin-4-yl, 1,1-dioxotetrahydro-4H-1,4-thiazin-4-yl, 1-piperidinyl, 1-homopiperidinyl, 1-piperazinyl and 1-homopiperazinyl, or from a group of the formula:

wherein X³ is a direct bond or is selected from O, NH and N(Me) and Q⁴ is phenyl, 2- or 3-furyl, 2- or 3-thienyl, 1- or 2-imidazolyl, 2-, 4- or 5-oxazolyl, 2-, 4- or 5-thiazolyl, 2-, 3- or 4-pyridyl, 3- or 4-pyridazinyl, 2- or 4-pyrimidinyl or 2-pyrazinyl, and any Q⁴ group optionally bears 1 or 2 substituents, which may be the same or different, selected from fluoro, chloro, bromo, trifluoromethyl, hydroxy, amino, methyl, ethyl, methoxy, ethoxy, methylamino, ethylamino, dimethylamino and diethylamino, and wherein any heterocyclyl group within $Q^1$ optionally bears 1 or 2 oxo substituents, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

(m) $Q^1$ is optionally substituted with 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonyl-amino, 1-azetidinyl, 2- or 3-tetrahydrofuranyl, 3-pyrrolin-1-yl, 1-pyrrolidinyl, morpholino, tetrahydro-4H-1,4-thiazin-4-yl, 1,1-dioxotetrahydro-4H-1,4-thiazin-4-yl, 1-piperidinyl, 1-homopiperidinyl, 1-piperazinyl and 1-homopiperazinyl, and wherein any heterocyclyl group within $Q^1$ optionally bears 1 or 2 oxo substituents, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

(n) $Q^1$ is a phenyl group which is optionally substituted with 1, 2 or 3 substituents, which may be the same or different, selected from those defined in paragraphs (k) to (m) hereinbefore;

(o) $Q^1$ is a 5- or 6-membered monocyclic heteroaryl ring containing 1 oxygen heteroatom or 1 or 2 nitrogen heteroatoms and optionally containing a further heteroatom selected from nitrogen, oxygen and sulphur, and $Q^1$ is optionally substituted with 1, 2 or 3 substituents, which may be the same or different, selected from those defined in paragraphs (k) to (m) hereinbefore;

(p) $Q^1$ is a 9- or 10-membered bicyclic heteroaryl ring containing 1 oxygen heteroatom or 1 or 2 nitrogen heteroatoms and optionally containing a further heteroatom selected from nitrogen, oxygen and sulphur, and $Q^1$ is optionally substituted with 1, 2 or 3 substituents, which may be the same or different, selected from those defined in paragraphs (k) to (m) hereinbefore;

(q) $Q^1$ is a 13- or 14-membered tricyclic heteroaryl ring containing 1 oxygen heteroatom or 1 or 2 nitrogen heteroatoms and optionally containing a further heteroatom selected from nitrogen, oxygen and sulphur, and $Q^1$ is optionally substituted with 1, 2 or 3 substituents, which may be the same or different, selected from hydroxy, halogeno, trifluoromethyl, amino, (1–6C)alkyl, (1–6C) alkoxy, (1–6C)alkylamino and di-[(1–6C)alkyl]amino;

(r) $Q^1$ is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from those defined in paragraphs (k) to (m) hereinbefore;

(s) $Q^1$ is 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl or 2-pyrazinyl which optionally bears 1 or 2 substituents selected from those defined in paragraphs (l) and (m) hereinbefore;

(t) $Q^1$ is 2-, 3-, 5- or 6-benzofuranyl, 2-, 3-, 5- or 6-indolyl, 2-, 3-, 5- or 6-benzothiophenyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from those defined in paragraphs (l) and (m) hereinbefore; and (u) $Q^1$ is 1-, 2- or 3-carbazolyl, 1-, 2-, 3- or 4-dibenzofuranyl or 1-, 2-, 3- or 4-dibenzothiophenyl which optionally bears 1 or 2 substituents selected from those defined in paragraph (q) hereinbefore.

A preferred compound of the invention is a pyrimidine derivative of the Formula I wherein m is 0, 1, 2 or 3, and each $R^1$ group, which may be the same or different, is selected from hydroxy, fluoro, chloro, bromo, trifluoromethyl, amino, carbamoyl, methyl, ethyl, propyl, methoxy, ethoxy, propoxy, methylthio, methylsulphinyl, methylsulphonyl, methylamino, ethylamino, propylamino, isopropylamino, butylamino, allylamino, propargylamino, dimethylamino, diethylamino, dipropylamino, N-allyl-N-methylamino, N-methylcarbamoyl, N,N-dimethylcarbamoyl and acetamido, or from a group of the formula:

$$Q^2—X^1—$$

wherein $X^1$ is a direct bond or is selected from O, NH and N(Me) and $Q^2$ is benzyl, 2-furylmethyl, 3-furylmethyl, 2-thienylmethyl, 3-thienylmethyl, 1-imidazolylmethyl, 2-imidazolylmethyl, 2-imidazol-1-ylethyl, 3-imidazol-1-ylpropyl, 4-imidazol-1-ylbutyl, 2-oxazolylmethyl, 4-oxazolylmethyl, 5-oxazolylmethyl, 2-thiazolylmethyl, 4-thiazolylmethyl, 5-thiazolylmethyl, 1,2,3-triazol-1-ylmethyl, 2-(1,2,3-triazol-1-yl)ethyl, 3-(1,2,3-triazol-1-yl)propyl, 1,2,4-triazol-1-ylmethyl, 2-(1,2,4-triazol-1-yl)ethyl, 3-(1,2,4-triazol-1-yl)propyl, 2-pyridylmethyl, 3-pyridylmethyl, 4-pyridylmethyl, 2-pyrid-2-ylethyl, 2-pyrid-3-ylethyl, 2-pyrid-4-ylethyl, 3-pyrid-2-ylpropyl, 3-pyrid-3-ylpropyl, 3-pyrid-4-ylpropyl, pyrrolidin-1-yl, pyrrolidin-2-yl, pyrrolidin-3-yl, morpholino, tetrahydro-4H-1,4-thiazin-4-yl, 1,1-dioxotetrahydro-4H-1,4-thiazin-4-yl, piperidino, piperidin-2-yl, piperidin-3-yl, piperidin-4-yl, homopiperidin-1-yl, homopiperidin-2-yl, homopiperidin-3-yl, homopiperidin-4-yl, piperazin-1-yl, homopiperazin-1-yl, pyrrolidin-1-ylmethyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, pyrrolidin-3-ylmethyl, 2-pyrrolidin-3-ylethyl, 3-pyrrolidin-3-ylpropyl, imidazolidin-1-ylmethyl, 2-imidazolidin-1-ylethyl, 3-imidazolidin-1-ylpropyl, imidazolidin-2-ylmethyl, 2-imidazolidin-2-ylethyl, 3-imidazolidin-2-ylpropyl, morpholinomethyl, 2-morpholinoethyl, 3-morpholinopropyl, morpholin-2-ylmethyl, 2-morpholin-2-ylethyl, 3-morpholin-2-ylpropyl, morpholin-3-ylmethyl, 2-morpholin-3-ylethyl, 3-morpholin-3-ylpropyl, tetrahydro-4H-1,4-thiazin-4-ylmethyl, 2-(tetrahydro-4H-1,4-thiazin-4-yl)ethyl, 3-(tetrahydro-4H-1,4-thiazin-4-yl)propyl, 1,1-dioxotetrahydro-4H-1,4-thiazin-4-ylmethyl, 2-(1,1-dioxotetrahydro-4H-1,4-thiazin-4-yl)ethyl, 3-(1,1-dioxotetrahydro-4H-1,4-thiazin-4-yl)propyl, piperidinomethyl, 2-piperidinoethyl, 3-piperidinopropyl, piperidin-2-ylmethyl, 2-piperidin-2-ylethyl, 3-piperidin-2-ylpropyl, piperidin-3-ylmethyl, 2-piperidin-3-ylethyl, 3-piperidin-3-ylpropyl, piperidin-4-ylmethyl, 2-piperidin-4-ylethyl, 3-piperidin-4-ylpropyl, homopiperidin-1-ylmethyl, 2-homopiperidin-1-ylethyl, 3-homopiperidin-1-ylpropyl, homopiperidin-2-ylmethyl, 2-homopiperidin-2-ylethyl, 3-homopiperidin-2-ylpropyl, homopiperidin-3-ylmethyl, 2-homopiperidin-3-ylethyl, 3-homopiperidin-3-ylpropyl, homopiperidin-4-ylmethyl, 2-homopiperidin-4-ylethyl, 3-homopiperidin-4-ylpropyl, piperazin-1-ylmethyl, 2-piperazin-1-ylethyl, 3-piperazin-1-ylpropyl, piperazin-2-ylmethyl, 2-piperazin-2-ylethyl, 3-piperazin-2-ylpropyl, homopiperazin-1-ylmethyl, 2-homopiperazin-1-ylethyl, 3-homopiperazin-1-ylpropyl, homopiperazin-2-ylmethyl, 2-homopiperazin-2-ylethyl or 3-homopiperazin-2-ylpropyl, and wherein a single pair of adjacent carbon atoms in a (2–6C)alkylene chain within a $R^1$ substituent is optionally separated by the insertion of a group selected from O and NH, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy propoxy, isopropoxy, methoxycarbonyl, ethoxycarbonyl and tert-butoxycarbonyl, and wherein any heterocyclyl group within a substituent on $R^1$ optionally bears 1 or 2 oxo substituents, and wherein any $CH_2$ or $CH_3$ group within a $R^1$ substituent optionally bears on each said $CH_2$ or $CH_3$ group 1 or 2 methyl substituents or a substituent selected from hydroxy, amino, methoxy, ethoxy, methylsulphonyl, methylamino, ethylamino, dimethylamino and diethylamino;

each of n and p is 0;

$R^3$ is hydrogen or methyl; and $Q^1$ is phenyl, 2-furyl, 2-thienyl, 4-oxazolyl, 5-isoxazolyl, 2- or 4-imidazolyl, 3- or 4-pyrazolyl, 4-thiazolyl, 5-isothiazolyl, 2-, 3- or 4-pyridyl, 4-pyridazinyl, 4- or 5-pyrimidinyl, 2- or 6-benzofuranyl, 2- or 6-indolyl, 2- or 6-benzothiophenyl, 2- or 6-quinolyl or 2- or 4-dibenzofuranyl which optionally bears 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonylamino, 1-azetidinyl, 3-pyrrolin-1-yl, 1-pyrrolidinyl, morpholino, tetrahydro-4H-1,4-thiazin-4-yl, 1,1-dioxotetrahydro-4H-1,4-thiazin-4-yl, 1-piperidinyl, 1-homopiperidinyl, 1-piperazinyl and 1-homopiperazinyl, or from a group of the formula:

—$X^3$—$Q^4$ wherein $X^3$ is a direct bond or is selected from O, NH and N(Me) and $Q^4$ is phenyl, 2- or 3-furyl, 2- or 3-thienyl, 1- or 2-imidazolyl, 2-, 4- or 5-oxazolyl, 2-, 4- or 5-thiazolyl, 2-, 3- or 4-pyridyl, 3- or 4-pyridazinyl, 2- or 4-pyrimidinyl or 2-pyrazinyl, and any $Q^4$ group optionally bears 1 or 2 substituents, which may be the same or different, selected from fluoro, chloro, bromo, trifluoromethyl, hydroxy, amino, methyl, ethyl, methoxy, ethoxy, methylamino, ethylamino, dimethylamino and diethylamino, and wherein any heterocyclyl group within $Q^1$ optionally bears 1 or 2 oxo substituents, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester thereof.

A further preferred compound of the invention is a pyrimidine derivative of the Formula I wherein m is 0, 1 or 2 and each $R^1$ group, which may be the same or different, is selected from hydroxy, fluoro, chloro, bromo, trifluoromethyl, amino, carbamoyl, methyl, ethyl, propyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, N-methylcarbamoyl, N,N-dimethylcarbamoyl, acetamido, benzyloxy, benzylamino, N-benzyl-N-methylamino, 2-furylmethoxy, 3-furylmethoxy, 2-imidazol-1-ylethylamino, 3-imidazol-1-ylpropylamino, 2-(1,2,4-triazol-1-yl)ethylamino, 3-(1,2,4-triazol-1-yl)propylamino, 2-pyridylmethoxy, 3-pyridylmethoxy, 4-pyridylmethoxy, pyrrolidin-1-yl, pyrrolidin-3-yloxy, pyrrolidin-3-ylamino, N-methyl-N-(3-pyrrolidinyl)amino, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethoxy, 3-imidazolidin-1-ylpropoxy, imidazolidin-2-ylmethoxy, 2-imidazolidin-2-ylethoxy, 3-imidazolidin-2-ylpropoxy, 2-imidazolidin-1-ylethylamino, 3-imidazolidin-1-ylpropylamino, 2-imidazolidin-2-ylethylamino, 3-imidazolidin-2-ylpropylamino, 2-morpholinoethoxy, 3-morpholinopropoxy, 2-morpholinoethylamino, 3-morpholinopropylamino, morpholin-2-ylmethoxy, 2-morpholin-2-ylethoxy, 3-morpholin-2-ylpropoxy, 2-morpholin-2-ylethylamino, 3-morpholin-2-ylpropylamino, morpholin-3-ylmethoxy, 2-morpholin-3-ylethoxy, 3-morpholin-3-ylpropoxy, 2-morpholin-3-ylethylamino, 3-morpholin-3-ylpropylamino, 2-piperidinoethoxy, 3-piperidinopropoxy, 2-piperidinoethylamino, 3-piperidinopropylamino, piperidin-2-ylmethoxy, 2-piperidin-2-ylethoxy, 3-piperidin-2-ylpropoxy, piperidin-2-ylmethylamino, 2-piperidin-2-ylethylamino, 3-piperidin-2-ylpropylamino, piperidin-3-ylmethoxy, 2-piperidin-3-ylethoxy, 3-piperidin-3-ylpropoxy, piperidin-3-ylmethylamino, 2-piperidin-3-ylethylamino, 3-piperidin-3-ylpropylamino, piperidin-4-ylmethoxy, 2-piperidin-4-ylethoxy, 3-piperidin-4-ylpropoxy, piperidin-4-ylmethylamino, 2-piperidin-4-ylethylamino, 3-piperidin-4-ylpropylamino, 2-homopiperidin-1-ylethoxy, 3-homopiperidin-1-ylpropoxy, 2-homopiperidin-1-ylethylamino, 3-homopiperidin-1-ylpropylamino, homopiperidin-2-ylmethoxy, homopiperidin-2-ylmethylamino, homopiperidin-3-ylmethoxy, homopiperidin-3-ylmethylamino, homopiperidin-4-ylmethoxy, homopiperidin-4-ylmethylamino, 2-piperazin-1-ylethoxy, 3-piperazin-1- ylpropoxy, 2-piperazin-1-ylethylamino, 3-piperazin-1-ylpropylamino, piperazin-2-ylmethoxy, piperazin-2-ylmethylamino, 2-piperazin-2-ylethoxy, 3-piperazin-2-ylpropoxy, 2-piperazin-2-ylethylamino, 3-piperazin-2-ylpropylamino, 2-homopiperazin-1-ylethoxy, 3-homopiperazin-1-ylpropoxy, 2-homopiperazin-1-ylethylamino, 3-homopiperazin-1-ylpropylamino, homopiperazin-2-ylmethoxy or homopiperazin-2-ylmethylamino, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy propoxy, isopropoxy, methoxycarbonyl, ethoxycarbonyl and tert-butoxycarbonyl, and wherein any heterocyclyl group within a substituent on $R^1$ optionally bears 1 or 2 oxo substituents, and wherein any $CH_2$ or $CH_3$ group within a $R^1$ substituent optionally bears on each said $CH_2$ or $CH_3$ group 1 or 2 methyl substituents or a substituent selected from hydroxy, amino, methoxy, ethoxy, methylsulphonyl, methylamino, ethylamino, dimethylamino and diethylamino;

each of n and p is 0;

$R^3$ is methyl; and $Q^1$ is phenyl or 3- or 4-pyridyl which optionally bears 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonylamino, 1-azetidinyl, 3-pyrrolin-1-yl, 1-pyrrolidinyl, morpholino, 1-piperidinyl, 1-homopiperidinyl, 1-piperazinyl and 1-homopiperazinyl, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester thereof.

A more preferred compound of the invention is a pyrimidine derivative of the Formula I wherein m is 0, 1 or 2 and each $R^1$ group, which may be the same or different, is selected from fluoro, chloro, bromo, amino, carbamoyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, pyrrolidin-3-yloxy, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethylamino, 3-imidazolidin-1-ylpropylamino, 2-morpholinoethoxy, 3-morpholinopropoxy, 2-morpholinoethylamino, 3-morpholinopropylamino, 2-piperidinoethoxy, 3-piperidinopropoxy, 2-piperidinoethylamino, 3-piperidinopropylamino, piperidin-3-ylmethoxy, piperidin-4-ylmethoxy, 2-piperazin-1-ylethoxy, 3-piperazin-1-ylpropoxy, 2-piperazin-1-ylethylamino, 3-piperazin-1-ylpropylamino or piperazin-2-ylmethoxy, and wherein any heterocyclyl group within a substituent on $R^1$ optionally bears 1 or 2 substituents, which may be the same or different, selected from hydroxy, fluoro, chloro, methyl, ethyl, propyl, isopropyl, methoxy, ethoxy, methoxycarbonyl, ethoxycarbonyl and tert-butoxycarbonyl, and wherein any heterocyclyl group within a substituent on $R^1$ optionally bears an oxo substituent, and wherein any $CH_2$ or $CH_3$ group within a $R^1$ substituent optionally bears on each said $CH_2$ or $CH_3$ group 1 or 2 methyl substituents or a substituent selected from hydroxy, amino, methylamino, ethylamino, dimethylamino and diethylamino;

each of n and p is 0;

$R^3$ is methyl; and $Q^1$ is phenyl or 4-pyridyl which optionally bears 1, 2 or 3 substituents, which may be the same or different, selected from fluoro, chloro, trifluoromethyl, amino, methyl, methoxy, methylamino, ethylamino, dimethylamino, diethylamino, 1-pyrrolidinyl, morpholino, piperidino, 1-homopiperidinyl, 1-piperazinyl and 1-homopiperazinyl, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester thereof.

A further more preferred compound of the invention is a pyrimidine derivative of the Formula I wherein m is 1 or 2 and each $R^1$ group, which may be the same or different, is selected from chloro, carbamoyl, 3-dimethylaminopropoxy, 3-dimethylamino-2,2-dimethylpropoxy, methylthio, 3-diethylaminopropylamino, 3-dimethylamino-2,2-dimethylpropylamino, 3-dimethylamino-2-hydroxypropylamino, N-isopropylpyrrolidin-3-yloxy, piperidin-4-yloxy, N-methylpiperidin-4-yloxy, N-ethylpiperidin-3-ylamino, N-methylpiperidin-4-ylamino, N-methyl-N-(N-methylpiperidin-4-yl)amino, 3-pyrrolidin-1-ylpropylamino, N-methylpyrrolidin-2-ylmethoxy, 2-(N-methylpyrrolidin-2-yl)ethoxy, 2-(N-methylpyrrolidin-2-yl)ethylamino, N-methylpiperidin-3-ylmethoxy and N,N'-dimethylpiperazin-2-ylmethoxy;

each of n and p is 0;

$R^3$ is methyl; and $Q^1$ is phenyl which bears 1 or 2 substituents, which may be the same or different, selected from fluoro, trifluoromethyl, dimethylamino, 1-pyrrolidinyl, morpholino, piperidino, 1-homopiperidinyl, 1-piperazinyl and 1-homopiperazinyl, or $Q^1$ is 4-pyridyl which bears 1 substituent selected from dimethylamino, 1-pyrrolidinyl, morpholino, piperidino, 1-homopiperidinyl, 1-piperazinyl and 1-homopiperazinyl, or a pharmaceutically acceptable salt or in-vivo-cleavable ester thereof.

A more preferred compound of the invention is a pyrimidine derivative of the Formula I wherein m is 0, 1 or 2 and each $R^1$ group, which may be the same or different, is selected from fluoro, chloro, bromo, amino, carbamoyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, pyrrolidin-3-yloxy, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethylamino, 3-imidazolidin-1-ylpropylamino, 2-morpholinoethoxy, 3-morpholinopropoxy, 2-morpholinoethylamino, 3-morpholinopropylamino, 2-piperidinoethoxy, 3-piperidinopropoxy, 2-piperidinoethylamino, 3-piperidinopropylamino, piperidin-3-ylmethoxy, piperidin-4-ylmethoxy, 2-piperazin-1-ylethoxy, 3-piperazin-1-ylpropoxy, 2-piperazin-1-ylethylamino, 3-piperazin-1-ylpropylamino or piperazin-2-ylmethoxy, and wherein any heterocyclyl group within a substituent on $R^1$ optionally bears 1 or 2 substituents, which may be the same or different, selected from hydroxy, fluoro, chloro, methyl, ethyl, propyl, isopropyl, methoxy, ethoxy, methoxycarbonyl, ethoxycarbonyl and tert-butoxycarbonyl, and wherein any heterocyclyl group within a substituent on $R^1$ optionally bears an oxo substituent, and wherein any $CH_2$ or $CH_3$ group within a $R^1$ substituent optionally bears on each said $CH_2$ or $CH_3$ group 1 or 2 methyl substituents or a substituent selected from hydroxy, amino, methylamino, ethylamino, dimethylamino and diethylamino;

each of n and p is 0;
$R^3$ is methyl; and
$Q^1$ is 4-dibenzofuranyl which optionally bears 1 or 2 substituents, which may be the same or different, selected from fluoro, chloro, trifluoromethyl, amino, methyl, methoxy, methylamino, ethylamino, dimethylamino and diethylamino;
or a pharmaceutically acceptable salt or in-vivo-cleavable ester thereof.

A further more preferred compound of the invention is a pyrimidine derivative of the Formula I
wherein m is 1 and the $R^1$ group is selected from chloro, carbamoyl, methoxy, ethoxy, 3-dimethylaminopropoxy, 3-dimethylamino-2,2-dimethylpropoxy, methylthio, N-isopropylpyrrolidin-3-yloxy, piperidin-4-yloxy, N-methylpiperidin-4-yloxy, N-ethylpiperidin-4-yloxy, N-propylpiperidin-4-yloxy, N-methylpyrrolidin-2-ylmethoxy, 2-(N-methylpyrrolidin-2-yl)ethoxy, N-methylpiperidin-3-ylmethoxy and N,N'-dimethylpiperazin-2-ylmethoxy;
each of n and p is 0;
$R^3$ is methyl; and
$Q^1$ is 4-dibenzofuranyl which optionally bears 1 or 2 substituents, which may be the same or different, selected from fluoro, chloro, trifluoromethyl and dimethylamino, or a pharmaceutically acceptable salt or in-vivo-cleavable ester thereof.

A particular preferred compound of the invention is, for example:—6-carbamoyl-2-chloro-4-[5-(3-fluoro-5-morpholinobenzamido)-2-methylanilino]pyrimidine, 4-[5-(3-fluoro-5-morpholinobenzamido)-2-methylanilino]-2-methylthiopyrimidine, 2-chloro-4-[2-methyl-5-(2-morpholinopyrid-4-ylcarbonylamino)anilino]pyrimidine, 4-[2-methyl-5-(2-morpholinopyrid-4-ylcarbonylamino)anilino]-2-(N-methylpiperidin-4-yloxy)pyrimidine, 2-(3-dimethylaminopropoxy)-4-[2-methyl-5-(2-morpholinopyrid-4-ylcarbonylamino)anilino]pyrimidine, 2-(3-dimethylamino-2,2-dimethylpropoxy)-4-[2-methyl-5-(2-morpholinopyrid-4-ylcarbonylamino)anilino]pyrimidine, 4-[2-methyl-5-(2-morpholinopyrid-4-ylcarbonylamino)anilino]-2-(N-methylpiperidin-3-ylmethoxy)pyrimidine, 2-[N-methyl-N-(N-methylpiperidin-4-yl)amino]-4-[2-methyl-5-(2-morpholinopyrid-4-ylcarbonylamino)anilino]pyrimidine and 4-[2-methyl-5-(2-morpholinopyrid-4-ylcarbonylamino)anilino]-2-[2-N-methylpyrrolidin-2-yl)ethylamino]pyrimidine;

or a pharmaceutically acceptable salt or in-vivo-cleavable ester thereof.

A further particular preferred compound of the invention is, for example:—2-(3-dimethylamino-2,2-dimthylpropoxy)-4-[5-(3-fluoro-5-morpholinobenzamido)-2-methylanilino]pyrimidine, 4-[5-(3-fluoro-5-morpholinobenzamido)-2-methylanilino]-2-(N-methylpiperidin-4-yloxy)pyrimidine, 4-[5-(3-fluoro-5-morpholinobenzamido)-2-methylanilino]-2-(N-propylpiperidin-4-yloxy)pyrimidine, 4-[5-(4-dibenzofuranylcarbonylamino)-2-methylanilino]-2-(N-methylpiperidin-4-yloxy)pyrimidine and 4-[5-(4-dibenzofuranylcarbonylamino)-2-methylanilino]-2-(3-dimethylamino-2,2-dimethylpropoxy)pyrimidine;

or a pharmaceutically acceptable salt or in-vivo-cleavable ester thereof.

A pyrimidine derivative of the Formula I, or a pharmaceutically-acceptable salt or in-vivo-cleavable ester thereof, may be prepared by any process known to be applicable to the preparation of chemically-related compounds. Such processes, when used to prepare a novel pyrimidine derivative of the Formula I are provided as a further feature of the invention and are illustrated by the following representative process variants in which, unless otherwise stated, $R^1$, m, $R^2$, n, $R^3$, p and $Q^1$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting an aniline of the Formula II

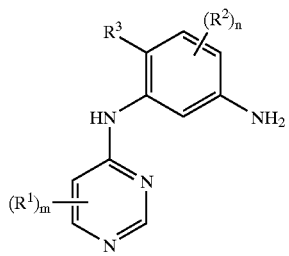

II with an acid of the Formula III, or a reactive derivative thereof,

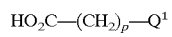

III under standard amide bond forming conditions, wherein variable groups are as defined hereinbefore and wherein any functional groups are protected if necessary, and
(i) removing any protecting groups; and
(ii) optionally forming a pharmaceutically-acceptable salt or in-vivo-cleavable ester.

A suitable activated derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl)silyl groups (for example trimethylsilyl and tert-butyldimethylsilyl); tri(lower alkyl) silyl lower alkyl groups (for example trimethylsilylethyl); and (2–6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley &

Sons 1992, for general guidance on reaction conditions and reagents. The reader is referred to Protective Groups in Organic Synthesis, 2nd Edition, by Green e al., published by John Wiley & Sons for general guidance on protecting groups.

The aniline of Formula II may be prepared by reduction of the corresponding nitro compound of Formula IV.

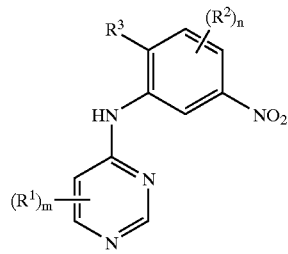

IV

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The nitro compound of Formula IV may be prepared by the reaction, conveniently in the presence of a suitable base as defined hereinbefore, of an activated heteroaryl compound of the Formula V

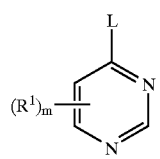

V wherein L is a displaceable group as defined hereinafter with an aniline of the Formula VI

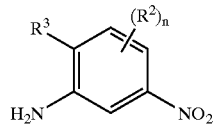

VI

A suitable displaceable group L is, for example, a halogeno group such as fluoro, chloro or bromo, an activated phenoxy group such as pentafluorophenoxy, a (1–6C) alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 50 to 150° C.

(b) A compound of the Formula I, or a pharmaceutically-acceptable salt or in-vivo-cleavable ester thereof, may be prepared by the reaction, conveniently in the presence of a suitable base as defined hereinbefore, of an activated heteroaryl compound of the Formula V

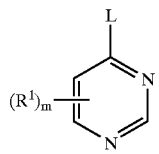

V wherein L is a displaceable group as defined hereinbefore, with an aniline of the Formula VII

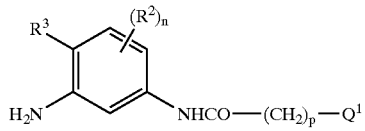

VII wherein variable groups are as defined hereinbefore and wherein any functional group is protected if necessary, and (i) removing any protecting groups; and (ii) optionally forming a pharmaceutically-acceptable salt or in-vivo-cleavable ester.

The reaction is conveniently carried out in the presence of a suitable inert diluent or carrier as defined hereinbefore and at a temperature in the range, for example, 20 to 200° C., conveniently in the range 50 to 150° C.

The aniline of Formula VII may be prepared by reduction of the corresponding nitro compound of Formula VIII.

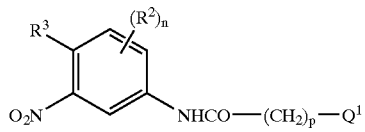

VIII under typical reaction conditions such as catalytic reduction with hydrogen gas in the presence of a metallic catalyst, for example palladium-on-carbon, or the use of ammonium formate in the presence of a metallic catalyst, for example palladium-on-carbon.

The nitro compound of the Formula VIII may be prepared by the coupling of an aniline of the Formula IX

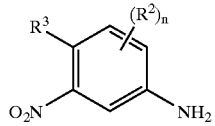

IX with an acid of the Formula III, or a reactive derivative thereof as defined hereinbefore,

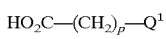

III under standard amide bond forming conditions as defined hereinbefore.

(c) A compound of the Formula I, or a pharmaceutically-acceptable salt or in-vivo-cleavable ester thereof, wherein $R^1$ or a substituent on $Q^1$ is an amino, (1–6C)alkylamino, di-[(1–6C)alkyl]amino, substituted (1–6C)alkylamino, substituted di-[(1–6C)alkyl]amino, a N-linked heterocyclyl substituent or a heterocyclylamino substituent may be prepared by the reaction, conveniently in the presence of a suitable base as defined hereinbefore, of an appropriate amine with a pyrimidine derivative of the Formula I wherein $R^1$ or a substituent on $Q^1$ as appropriate is a suitable displaceable group as defined hereinbefore and wherein other variable groups are as defined hereinbefore and wherein any functional group is protected if necessary, and (i) removing any protecting groups; and (ii) optionally forming a pharmaceutically-acceptable salt or in-vivo-cleavable ester.

The reaction is conveniently carried out in the presence of a suitable inert diluent or carrier as defined hereinbefore and at a temperature in the range, for example, 20 to 200° C., conveniently in the range 75 to 150° C.

(d) A compound of the Formula I, or a pharmaceutically-acceptable salt or in-vivo-cleavable ester thereof, wherein $R^1$ or a substituent on $Q^1$ is a (1–6C)alkoxy or substituted (1–6C)alkoxy substituent or a heterocyclyloxy substituent may be prepared by the reaction, conveniently in the presence of a suitable base as defined hereinbefore, of an appropriate alcohol with a pyrimidine derivative of the Formula I wherein $R^1$ or a substituent on $Q^1$ as appropriate is a suitable displaceable group as defined hereinbefore and wherein other variable groups are as defined hereinbefore and wherein any functional group is protected if necessary, and (i) removing any protecting groups; and (ii) optionally forming a pharmaceutically-acceptable salt or in-vivo-cleavable ester.

The reaction is conveniently carried out in the presence of a suitable inert diluent or carrier as defined hereinbefore and at a temperature in the range, for example, 20 to 200° C., conveniently in the range 100 to 180° C.

(e) A compound of the Formula I, or a pharmaceutically-acceptable salt or in-vivo-cleavable ester thereof, wherein m is 0 may be prepared by the cleavage, conveniently in the presence of a suitable metallic catalyst as defined hereinbefore, of a compound of the Formula I, wherein m is 1, 2 or 3 and each $R^1$ substituent is a halogeno group and wherein other variable groups are as defined hereinbefore and wherein any functional group is protected if necessary, and (i) removing any protecting groups; and (ii) optionally forming a pharmaceutically-acceptable salt or in-vivo-cleavable ester.

The reaction is conveniently carried out in the presence of a suitable inert diluent or carrier as defined hereinbefore and at a temperature in the range, for example, 20 to 200° C., conveniently in the range 20 to 200° C.

(f) A compound of the Formula I, or a pharmaceutically-acceptable salt or in-vivo-cleavable ester thereof, wherein $R^1$ or $Q^1$ contains a (1–6C)alkoxy or substituted (1–6C) alkoxy group or a (1–6C)alkylamino or substituted (1–6C)alkylamino group may be prepared by the alkylation, conveniently in the presence of a suitable base as defined hereinbefore, of a pyrimidine derivative of the Formula I wherein $R^1$ or $Q^1$ contains a hydroxy group or a primary or secondary amino group as appropriate, and wherein other variable groups are as defined hereinbefore and wherein any functional group is protected if necessary, and (i) removing any protecting groups; and (ii) optionally forming a pharmaceutically-acceptable salt or in-vivo-cleavable ester.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ or $Q^1$ contains a (1–6C) alkylamino or substituted (1–6C)alkylamino group, a reductive amination reaction may be employed. For example, for the production of those compounds of the Formula I wherein $R^1$ or $Q^1$ contains a N-methyl group, the corresponding compound containing a N—H group may be reacted with formaldehyde in the presence of a suitable reducing agent. A suitable reducing agent is, for example, a hydride reducting agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) A compound of the Formula I, or a pharmaceutically-acceptable salt or in-vivo-cleavable ester thereof, wherein $R^1$ is a hydroxy group may be prepared by the cleavage, conveniently in the presence of a suitable acidic catalyst, of a compound of the Formula I, wherein $R^1$ is a halogeno group and wherein other variable groups are as defined hereinbefore and wherein any functional group is protected if necessary, and (i) removing any protecting groups; and (ii) optionally forming a pharmaceutically-acceptable salt or in-vivo-cleavable ester.

A suitable acidic catalyst is, for example, an inorganic or organic acid such as hydrochloric, hydrobromic, sulphuric, formic, acetic, trifluoroacetic, citric or maleic acid.

The reaction is conveniently carried out in the presence of a suitable inert diluent or carrier as defined hereinbefore and at a temperature in the range, for example, 20 to 200° C., conveniently in the range 20 to 100° C.

(h) A compound of the Formula I, or a pharmaceutically-acceptable salt or in-vivo-cleavable ester thereof, wherein $R^1$ is a (1–6C)alkylsulphinyl or (1–6C)alkylsulphonyl group may be prepared by the oxidation, conveniently in the presence of a suitable metal salt catalyst, of a compound of the Formula I, wherein $R^1$ is a (1–6C)alkylthio group and wherein other variable groups are as defined hereinbefore and wherein any functional group is protected if necessary, and (i) removing any protecting groups; and (ii) optionally forming a pharmaceutically-acceptable salt or in-vivo-cleavable ester.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinium.

A suitable metal salt catalyst is, for example, a tungsten-containing salt such as sodium tungstate.

The oxidation is generally carrried out under as mild conditions as possible and with the required stoichiometric amount of oxidising agent in order to reduce the risk of over oxidation and damage to other functional groups.

In general the reaction is carried out in a suitable solvent or diluent such as methylene chloride, chloroform, acetone, tetrahydrofuran, tert-butyl methyl ether, N,N-dimethylformamide or N,N-dimethylacetamide and at a temperature in the range, for example, −25 to 150° C., conveniently at or near ambient temperature, that is in the range 15 to 35° C.

When a compound carrying a sulphinyl group is required a milder oxidising agent may also be used, for example sodium or potassium metaperiodate, conveniently in a polar solvent such as acetic acid or ethanol. It will be appreciated that when a compound of the Formula I containing a (1–6C)alkylsulphonyl group is required, it may be obtained by oxidation of the corresponding (1–6C)alkylsulphinyl compound as well as of the corresponding (1–6C)alkylthio compound.

The following biological assays and Examples serve to illustrate the present invention.

Biological Assays

The following assays can be used to measure the p38 kinase-inhibitory, the TNF-inhibitory and anti-arthritic effects of the compounds of the present invention:

In Vitro Enzyme Assay

The ability of compounds of the invention to inhibit the enzyme p38 kinase was assessed. Activity of test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886–2891. p38β (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated *coli*-expressed MKK6 retained sufficient activity to fully activate both isoforms of p38. The activation incubate comprised p38β (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-Based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5% CO$_2$/95% air) incubator (Falcon 3072; 96 well flat-bottom tissue culture plates). 20 μl lipopolysaccharide [LPS *E. Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

% inhibition=(*LPS* alone−medium alone)−(test concentration−medium alone)×100(*LPS* alone−medium alone)

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

% inhibition of *TNFα*=Mean *TNFα* (Controls)−Mean *TNFα* (Treated)×100 Mean *TNFα* (Controls)

Alternatively, mice could be used instead of rats in the above procedure.

Test as Anti-Arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146, 857.
2. Williams, R. O. et al., (1992) *Proc. Natl. Acad. Sci.*, 89, 9784.
3. Williams, R. O. et al., (1995) *Immunology*, 84, 433.
4. Badger, M. B. et al., (1996) *The Journal of Pharmacology and Experimental Therapeutics*, 279, 1453–1461.

Although the pharmacological properties of the compounds of the Formula I vary with structural change as expected, in general a compound of the Formula I gives over 30% inhibition of p38α and/or p38β at concentrations up to 10 μM and over 30% inhibition in the PBMC test at concentrations up to 50 μM. No physiologically unacceptable toxicity was observed at the effective dose for compounds tested of the present invention.

By way of example:—6-carbamoyl-2-chloro-4-[5-(3-fluoro-5-morpholinobenzamido)-2-methylanilino]pyrimidine has an $IC_{50}$ of approximately 0.03 μM against p38α and an $IC_{50}$ of approximately 16 μM in the Human Whole Blood test.

According to a further aspect of the invention there is provided a pharmaceutical composition which comprises a pyrimidine derivative of the Formula I, or a pharmaceutically-acceptable or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided a pyrimidine derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of a pyrimidine derivative of the Formula I, or a pharmaceutically-acceptable salt or in-vivo-cleavable ester thereof, as defined hereinbefore in the manufacture of a medicament for use in the treatment or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as a COX-1 inhibitor, for example indomethacin, ketorolac, acetylsalicyclic acid, ibuprofen, sulindac, tolmetin or piroxicam, or a COX-2 inhibitor, for example celecoxib or rofecoxib. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:—
DMF N,N-dimethylformamide
DMSO dimethylsulphoxide
THF tetrahydrofuran
DMA N,N-dimethylacetamide.

EXAMPLE 1

6-Carbamoyl-2-chloro-4-[5-(3-fluoro-5-morpholino-benzamido)-2-methylanilino]-pyrimidine A mixture of N-(3-amino-4-methylphenyl)-3-fluoro-5-morpholinobenzamide (0.33 g), 6-carbamoyl-2,4-dichloropyrimidine (0.212 g), N,N-di-isopropylethylamine (0.53 ml) and n-butanol (5 ml) was stirred and heated to reflux for 36 hours. Water and isohexane were added and the precipitated product was isolated and dried. There was thus obtained the title compound (0.059 g); NMR Spectrum: (DMSOd$_6$) 2.14 (s, 3H), 3.23 (m, 4H), 3.72 (m, 4H), 6.97 (d, 1H), 7.12 (d, 1H), 7.29 (m, 2H), 7.6 (d, 1H), 7.74 (s, 1H), 7.81 (s, 1H), 7.92 (s, 1H), 9.9 (s, 1H), 10.21 (s, 1H); Mass Spectrum: M–H' 483 & 485.

The N-(3-amino-4-methylphenyl)-3-fluoro-5-morpholinobenzamide used as a starting material was obtained as follows:—

A solution of 3,5-difluorobenzoyl chloride (2.82 g) in methylene chloride (20 ml) was added to a stirred mixture of 4-methyl-3-nitroaniline (2.28 g), triethylamine (4.35 ml) and methylene chloride (80 ml). The resultant mixture was stirred at ambient temperature for 16 hours. The precipitate was isolated, washed with methylene chloride and dried. There was thus obtained N-(4-methyl-3-nitrophenyl)-3,5-difluorobenzamide; NMR Spectrum: (DMSOd$_6$) 2.43 (s, 3H), 7.43 (m, 2H), 7.63 (m, 2H), 7.95 (m, 2H), 8.43 (d, 1H), 10.42 (s, 1H); Mass Spectrum: M+H$^+$ 293.

A mixture of a portion (1 g) of the material so obtained and morpholine (5 ml) was stirred and heated to 100° C. for 48 hours and then to 120° C. for 24 hours. The reaction mixture was cooled and poured into water (100 ml). The resultant solid was isolated, washed with water and dried. The material so obtained was purified by column chromatography on silica using a 1:1 mixture of isohexane and ethyl acetate as eluent. There was thus obtained N-(4-methyl-3-nitrophenyl)-3-fluoro-5-morpholinobenzamide as a solid (0.53 g); NMR Spectrum: (DMSOd$_6$) 2.46 (s, 3H), 3.22 (t, 4H), 3.75 (t, 4H), 6.98 (m, 1H), 7.12 (d, 1H), 7.27 (s, 1H), 7.46 (d, 1H), 7.96 (m, 1H), 8.43 (d, 1H), 10.48 (s, 1H); Mass Spectrum: M+H$^+$ 360.

A portion (0.483 g) of the compound so obtained was dissolved in ethyl acetate (40 ml) and hydrogenated over 10% palladium-on-carbon catalyst (0.6 g) under an atmosphere of hydrogen until the uptake of hydrogen ceased. The catalyst was removed by filtration and the filtrate was evaporated. The residue was triturated under diethyl ether (25 ml). The resultant solid was collected, washed with diethyl ether and dried. There was thus obtained the required starting material (0.341 g); NMR Spectrum: (DMSOd$_6$) 1.99 (s, 3H), 3.19 (t, 4H), 3.76 (t, 4H), 4.8 (s, 2H), 6.75 (d, 1H), 6.82 (d, 1H), 6.9 (d, 1H), 7.02 (s, 1H), 7.04 (d, 1H), 7.23 (s, 1H), 9.81 (s, 1H).

EXAMPLE 2

Using an analogous procedure to that described in Example 1, the appropriate 4-chloropyrimidine was reacted with the appropriate aniline to give the compounds described in the following table. Unless otherwise stated, each aniline starting material is either commercially available or is readily prepared by standard methods from known materials.

TABLE I

| No. | (R$^1$)$_m$ | (R$^4$)$_p$ | Note |
|---|---|---|---|
| 1 | 2-chloro | 3-fluoro-5-morpholino | (a) |
| 2 | 2-methylthio | 3-fluoro-5-morpholino | (b) |
| 3 | 6-chloro | 3-fluoro-5-morpholino | (c) |
| 4 | 6-chloro | 3-morpholino | (d) |
| 5 | 6-chloro | 3-dimethylamino | (e) |
| 6 | 2-chloro | 3-morpholino | (f) |
| 7 | 2-methoxyethoxy | 3-fluoro-5-morpholino | (g) |

Notes
(a) The reaction mixture was evaporated and the residue was purified by column chromatography on silica using increasingly polar mixtures of isohexane and ethyl acetate as eluent. The product so obtained gave the following data: NMR Spectrum: (DMSOd$_6$) 2.15 (s, 3H), 3.2 (m, 4H), 3.72 (m, 4H), 6.48 (d, 1H), 6.95 (m, 1H), 7.1 (m, 1H), 7.27 (m, 2H), 7.56 (m, 1H), 7.71 (m, 1H), 8.08 (d, 1H), 9.56 (s, 1H), 10.16 (s, 1H); Mass Spectrum: M+H$^+$ 442.
(b) The reaction mixture was heated to reflux for 24 hours. The resultant mixture was evaporated and the residue was purified by column chromatography on silica using a 19:1 mixture of methylene chloride and methanol as eluent. The product so obtained gave the following data: NMR Spectrum: (DMSOd$_6$) 2.16 (s, 3H), 2.37 (s, 3H), 3.21 (m, 4H), 3.74 (m, 4H), 6.29 (d, 1H), 6.96 (m, 1H), 7.1 (m, 1H), 7.25 (m, 2H), 7.5 (m, 1H), 7.82 (m, 1H), 8.03 (m, 1H), 9.04 (s, 1H), 10.13 (s, 1H); Mass Spectrum: M+H$^+$ 454.
(c) The reaction mixture was evaporated and the residue was purified by column chromatography on silica using increasingly polar mixtures of isohexane and ethyl acetate as eluent. The product so obtained gave the following data: NMR Spectrum: (DMSOd$_6$) 2.15 (s, 3H), 3.2 (m, 4H), 3.72 (m, 4H), 6.56 (s, 1H), 6.95 (m, 1H), 7.1 (m, 1H), 7.26 (m, 1H), 7.27 (s, 1H), 7.56 (m, 1H), 7.76 (m, 1H), 8.34 (s, 1H), 9.37 (s, 1H), 10.15 (s, 1H); Mass Spectrum: M+H$^+$ 442.
(d) The reaction mixture was evaporated and the residue was purified by column chromatography on silica using increasingly polar mixtures of methylene chloride and methanol as eluent. The product so obtained gave the following data: NMR Spectrum: (DMSOd$_6$) 2.17 (s, 3H), 3.18 (m, 4H), 3.79 (m, 4H), 6.57 (s, 1H), 7.18 (m, 1H), 7.27 (m, 1H), 7.47 (m, 2H), 7.44 (m, 1H), 7.6 (m, 1H), 7.78 (m, 1H), 8.36 (s, 1H), 9.68 (s, 1H), 10.13 (s, 1H); Mass Spectrum: M+H$^+$ 424.

The N-(3-amino-4-methylphenyl)-3-morpholinobenzamide used as a starting material was prepared as follows:—
A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris(dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried (MgSO$_4$) and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained, 5M sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR Spectrum: (DMSOd$_6$) 3.1 (t, 4H), 3.73 (t, 4H), 7.19 (d, 1H), 7.32 (d, 1H), 7.38 (t, 1H), 7.42 (s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); Mass Spectrum: M+H$^+$ 222.

A solution of 3-morpholinobenzoyl chloride (0.24 g) in methylene chloride (5 ml) was added to a stirred mixture of 4-methyl-3-nitroaniline (0.15 g), pyridine (0.24 ml) and methylene chloride (10 ml). The reaction mixture was stirred at ambient temperature for 16 hours. The organic phase was washed with water and with a saturated aqueous sodium bicarbonate solution. The organic layer was dried (MgSO$_4$) and evaporated. The residual solid was triturated under diethyl ether and the resultant solid was isolated and dried to give N-(3-nitro-4-methylphenyl)-3-morpholinobenzamide (0.28 g); NMR Spectrum: (DMSOd$_6$) 3.2 (t, 4H), 3.3 (s, 3H), 3.78 (t, 4H), 7.19 (s, 1H), 7.4 (m, 2H), 7.47 (d, 2H), 8.0 (d, 1H), 8.83 (s, 1H), 10.23 (s, 1H).

10% Palladium-on-carbon (0.035 g) was added to a stirred solution in methanol (40 ml) of the nitro compound so obtained (0.28 g) and the mixture was stirred at ambient temperature under 1 atmosphere pressure of hydrogen. After uptake of hydrogen had ceased, the catalyst was removed by filtration and the filtrate was evaporated to give N-(3-amino-4-methylphenyl)-3-morpholinobenzamide; NMR Spectrum: (DMSOd$_6$) 2.0 (s, 3H), 3.19 (t, 4H), 3.78 (t, 4H), 4.8 (s, 2H), 6.8 (q, 2H), 7.08 (s, 1H), 7.1 (d, 1H), 7.34 (m, 2H), 7.4 (s, 1H), 9.8 (s, 1H); Mass Spectrum: M+H$^+$ 312.
(e) The product gave the following data: NMR Spectrum: (DMSOd$_6$) 2.17 (s, 3H), 2.97 (s, 6H), 6.56 (m, 1H), 6.94 (m, 1H), 7.2–7.33 (m, 4H), 7.6 (m, 1H), 7.8 (m, 1H), 8.37 (s, 1H), 9.39 (s, 1H), 10.1 (s, 1H); Mass Spectrum: M+H$^+$ 382 & 384.

The N-(3-amino-4-methylphenyl)-3-dimethylaminobenzamide used as starting material was prepared as follows:

Oxalyl chloride (13.0 ml) was added dropwise to a stirred mixture of 3-dimethylaminobenzoic acid (20.3 g) and DMF (a few drops) which had been cooled to 0° C. The mixture was allowed to warm to ambient temperature and was stirred for 4 hours. The resultant mixture was evaporated and the residue was dissolved in methylene chloride (150 ml). 4-Methyl-3-nitroaniline (15.2 g) and triethylamine (27.9 ml) were added in turn and the resultant mixture was stirred at ambient temperature for 16 hours. The reaction mixture was washed in turn with water, with a saturated aqueous solution of sodium bicarbonate and with a saturated aqueous sodium chloride solution, dried over magnesium sulphate and evaporated. The residue was triturated under a mixture of ethyl acetate and isohexane. The solid so obtained was filtered off and recrystallised from ethanol to give N-(3-nitro-4-methylphenyl)-3-dimethylamino-benzamide (6.1 g); NMR Spectrum: (DMSOd$_6$) 2.46 (s, 3H), 2.95 (s, 6H), 6.92 (d, 1H), 7.22 (m, 2H), 7.32 (t, 1H), 7.45 (d, 1H), 7.97 (d, 1H), 8.53 (s, 1H), 10.43 (s, 1H).

After repetition of the previous reactions, a sample (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to give N-(3-amino-4-methylphenyl)-3-dimethylaminobenzamide (6.89 g); NMR Spectrum: (DMSOd$_6$) 2.0 (s, 3H), 2.94 (s, 6H), 4.78 (s, 2H), 6.82 (m, 3H), 7.07 (s, 1H), 7.17 (m, 2H), 7.25 (m, 1H), 9.74 (s, 1H).

(f) The reaction mixture was heated to reflux for 76 hours. The resultant mixture was evaporated and the residue was purified by column chromatography on silica using increasingly polar mixtures of isohexane and ethyl acetate as eluent. The product so obtained gave the following data: NMR Spectrum: (DMSOd$_6$) 2.14 (s, 3H), 3.17 (m, 4H), 3.75 (m, 4H), 6.49 (d, 1H), 7.13 (m, 1H), 7.24 (d, 1H), 7.36 (m, 21), 7.42 (m, 1H), 7.73 (m, 1H), 8.08 (d, 1H), 9.57 (s, 1H), 10.13 (s, 1H); Mass Spectrum: M+H$^+$ 424 and 426.

(g) A mixture of 4-chloro-2-(2-methoxyethoxy)pyrimidine and 2-chloro-4-(2-methoxyethoxy)pyrimidine was used. The reaction mixture was heated to reflux for 2 hours. The resultant mixture was evaporated and the residue was purified by column chromatography on silica using increasingly polar mixtures of methylene chloride and methanol as eluent. The required product gave the following data: NMR Spectrum: (DMSOd$_6$) 2.16 (s, 3H), 3.21 (m, 7H), 3.56 (m, 2H), 3.73 (m, 4H), 4.27 (m, 2H), 6.26 (d, 1H), 6.95 (m, 1H), 7.1 (m, 1H), 7.22 (d, 1H), 7.27 (s, 1H), 7.5 (m, 1H), 7.81 (s, 1H), 7.98 (d, 1H), 8.96 (s, 1H), 10.13 (s, 1H); Mass Spectrum: M+H$^+$ 482.

The mixture of 4-chloro-2-(2-methoxyethoxy)pyrimidine and 2-chloro-4-(2-methoxyethoxy)pyrimidine used as the starting materials was obtained as follows:— n-Butyl lithium (1.6M solution in hexane, 4.6 ml) was added dropwise to a stirred solution of 2-methoxyethanol (0.58 ml) in THF (20 ml) that had been cooled to −70° C. The resultant mixture was allowed to warm to ambient temperature over 30 minutes and was added to a stirred suspension of 2,4-dichloropyrimidine (1.0 g) in THF (20 ml) that had been cooled to −70° C. The resultant mixture was held at this temperature for 15 minutes and then stirred at ambient temperature for 18 hours. Diethyl ether (200 ml) was added and the mixture was washed in turn with water, a saturated aqueous sodium bicarbonate solution and brine. The organic solution was dried over sodium sulphate and evaporated. There was thus obtained a mixture of 4-chloro-2-(2-methoxyethoxy)pyrimidine and 2-chloro-4-(2-methoxyethoxy)pyrimidine as an oil (1.1 g) which was used without further purification; NMR Spectrum: (DMSOd$_6$) 3.28 (s, 3H), 3.65 (m, 2H), 4.23 (m, 2H), 7.0 (d, 0.4H), 7.3 (d, 0.6H), 8.44 (d, 0.4H), 8.56 (d, 0.6H); Mass Spectrum: M+H$^+$ 189.

EXAMPLE 3

5-Amino-6-chloro-4-[5-(3-fluoro-5-morpholinobenzamido) 2-methylanilino]pyrimidine Ethereal hydrogen chloride solution (1M, 1.5 ml) was added to a mixture of 5-amino-4,6-dichloropyrimidine (0.512 g), N-(3-amino-4-methylphenyl)-3-fluoro-5-morpholinobenzamide (0.514 g) and n-butanol (10 ml) and the resultant mixture was stirred and heated to reflux for 24 hours. Di-isopropylamine (1 ml) was added and the mixture was allowed to cool to ambient temperature. Water and a mixture of diethyl ether and isohexane were added and the precipitated solid was collected and dried. There was thus obtained the title compound (0.373 g); NMR Spectrum: 2.12 (s, 3H), 3.22 (m, 4H), 3.74 (m, 4H), 5.28 (s, 2H), 6.87 (d, 1H), 7.11 (d, 1H), 7.22 (d. 1H), 7.27 (s, 1H), 7.52 (d, 1H), 7.69 (s, 1H), 7.73 (s, 1H), 8.03 (s, 1H), 10.15 (s, 1H); Mass Spectrum: M−H$^−$ 455 & 457.

EXAMPLE 4

4-[2-Methyl-5-(3-morpholinobenzamido)anilino]pyrimidine

10% Palladium-on-carbon (0.02 g) was added to a mixture of 4-[2-methyl-5-(3-morpholinobenzamido)anilino]-6-chloropyrimidine (0.169 g), ammonium formate (0.165 g) and ethanol (5 ml) and the resultant mixture was stirred and heated to reflux for 18 hours. The catalyst was removed by filtration and the filtrate was evaporated. The residue was partitioned between methylene chloride and water and the organic phase was washed with brine, dried over sodium sulphate and evaporated. There was thus obtained the title compound (0.145 g); NMR Spectrum: (DMSOd$_6$) 2.23 (s, 3H), 3.24 (m, 4H), 3.83 (m, 4H), 6.68 (m, 1H), 7.2 (m, 1H), 7.3 (m, 1H), 7.43 (m, 2H), 7.5 (m, 1H), 7.61 (m, 1H), 7.88 (m, 1H), 8.28 (m, 1H), 8.57 (s, 1H), 9.06 (s, 1H), 10.18 (s, 1H); Mass Spectrum: M+H$^+$ 390.

EXAMPLE 5

4-[5-(3-dimethylaminobenzamido)-2-methylanilino]-6-(3-pyrrolidin-1-ylpropylamino)pyrimidine A mixture of 4-[5-(3-dimethylaminobenzamido)-2-methylanilino]-6-chloropyrimidine (0.114 g), 3-pyrrolidin-1-ylpropylamine (0.95 ml), N,N-di-isopropylethylamine (0.063 ml) and n-butanol (2 ml) was stirred and heated to reflux for 18 hours. The mixture was evaporated and the residue was purified by column chromatography on silica using a 10:1 mixture of ethyl acetate and methanol as eluent. There was thus obtained the title compound (0.124 g); NMR Spectrum: (DMSOd$_6$) 1.59 (m, 6H), 2.15 (s, 3H), 2.34 (m, 6H), 2.93 (s, 6H), 3.14 (m, 2H), 6.72 (m, 1H), 6.89 (m, 1H), 7.2 (m, 4H), 7.3 (m, 1H), 7.5 (m, 1H), 7.72 (m, 1H), 7.96 (m, 1H), 8.16 (s, 1H), 10.02 (s, 1H); Mass Spectrum: M+H$^+$ 474.

EXAMPLE 6

Using an analogous procedure to that described in Example 1, the appropriate 4-chloropyrimidine was reacted with the appropriate aniline to give the compounds described in the following table. Unless otherwise stated, each aniline starting material is either commercially available or is readily prepared by standard methods from known materials.

TABLE II

| No. | (R¹)ₘ | R⁴ | Note |
|---|---|---|---|
| 1 | 2-chloro | morpholino | (a) |
| 2 | 6-chloro | morpholino | (b) |
| 3 | 5-bromo-2-methylthio | morpholino | (c) |

Notes (a) The reaction mixture was evaporated and the residue was purified by column chromatography on silica using a 3:1 mixture of isohexane and ethyl acetate as eluent. The product so obtained gave the following data: NMR Spectrum: (DMSOd₆) 2.15 (s, 3H), 3.52 (m, 4H), 3.71 (m, 4H), 6.49 (m, 1H), 7.21 (s, 1H), 7.27 (m, 1H), 7.57 (m, 1H), 7.72 (m, 1H), 8.08 (m, 1H), 8.26 (m, 1H), 9.97 (s, 1H), 10.30 (s, 1H); Mass Spectrum: M+H⁺ 425 & 427.

The N-(3-amino-4-methylphenyl)-2-morpholinopyridine-4-carboxamide used as a starting material was prepared as follows:—

Triethylamine (31.8 ml) was added to a stirred mixture of 4-methyl-3-nitroaniline (15.8 g), 2-chloropyridine-4-carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus obtained 2-chloro-N-(4-methyl-3-nitrophenyl)pyridine-4-carboxamide (10.2 g). The organic filtrate was washed with a saturated aqueous sodium bicarbonate solution, dried over magnesium sulphate and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR Spectrum: (DMSOd₆) 2.48 (s, 3H), 7.51 (d, 1H), 7.86 (m, 1H), 7.96 (m, 2H), 8.49 (m, 1H), 8.64 (m, 1H), 10.85 (s, 1H); Mass Spectrum: M+H⁺ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR Spectrum: (DMSOd₆) 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H); Mass Spectrum: M+H⁺ 343.

A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino-4-methylphenyl)-2-morpholinopyridine-4-carboxamide (6.41 g); NMR Spectrum: (DMSOd₆) 2.01 (s, 3H), 3.52 (m, 4H), 3.73 (m, 4H), 4.83 (s, 2H), 6.78 (d, 1H), 6.84 (d, 1H) 7.04–7.08 (m, 2H), 7.2 (s, 1H), 8.24 (d, 1H), 9.95 (s, 1H); Mass Spectrum M+H⁺ 313.

(b) The reaction mixture was evaporated and the residue was purified by column chromatography on silica using increasingly polar mixtures of methylene chloride and methanol as eluent. The product so obtained gave the following data: NMR Spectrum: (DMSOd₆) 2.17 (s, 3H), 3.52 (m, 4H), 3.7 (m, 4H), 6.56 (s, 1H), 7.09 (m, 1H), 7.2 (m, 1H), 7.26 (m, 1H), 7.57 (m, 1H), 7.76 (m, 1H), 8.26 (m, 1H), 8.34 (s, 1H), 9.37 (s, 1H), 10.58 (s, 1H); Mass Spectrum: M+H⁺ 425.

(c) The reaction mixture was heated to reflux for 18 hours. The mixture was cooled to ambient temperature and an excess of 1M ethereal hydrogen chloride solution was added. The resultant mixture was heated to reflux for 24 hours. After cooling, isohexane was added and the precipitated solid was collected by filtration. The product was obtained as a hydrochloride salt and gave the following data: NMR Spectrum: (DMSOd₆) 2.12 (s, 3H), 2.21 (s, 3H), 3.64 (m, 4H), 3.73 (m, 4H), 7.19 (d, 1H), 7.28 (d, 1H), 7.53 (s, 1H), 7.6 (m, 1H), 7.8 (s, 1H), 8.23 (d, 1H), 8.35 (s, 1H), 8.92 (s, 1H), 10.57 (s, 1H); Mass Spectrum: M+H⁺ 515 & 517.

(d) The product gave the following data: NMR Spectrum: (DMSOd₆); Mass Spectrum: M+H⁺.

EXAMPLE 7

4-[2-Methyl-5-(2-morpholinopyrid-4-ylcarbonylamino)anilino]pyrimidine

Using an analogous procedure to that described in Example 4,6-chloro-4-[2-methyl-5-(2-morpholinopyrid-4-ylcarbonylamino)anilino]pyrimidine was reacted with ammonium formate to give the title compound as a solid in 100% yield; NMR Spectrum: (DMSOd₆) 2.23 (s, 3H), 3.57 (m, 4H), 3.77 (m, 4H), 6.68 (m, 1H), 7.16 (m, 1H), 7.29 (m, 1H), 7.3 (m, 1H), 7.59 (m, 1H), 7.88 (m, 1H), 8.28 (m, 1H), 8.33 (m, 1H), 8.55 (s, 1H), 9.09 (s, 1H), 10.36 (s, 1H); Mass Spectrum: M+H⁺ 391.

EXAMPLE 8

4-[2-Methyl-5-(2-morpholinopyrid-4-ylcarbonylamino)anilino]-2-(N-methylpiperidin-4-yloxy)pyrimidine A mixture of 2-chloro-4-[2-methyl-5-(2-morpholinopyrid-4-ylcarbonylamino)anilino]pyrimidine (0.13 g), 4-hydroxy-N-methylpiperidine (0.087 g) and potassium tert-butoxide (1M in tert-butanol, 1.5 ml) was stirred and heated to 140° C. for 1 hour. The mixture was partitioned between water and methylene chloride and the organic phase was washed with brine, dried over sodium sulphate and evaporated. There was thus obtained the title compound as a solid (0.11 g); NMR Spectrum: (DMSOd₆) 1.45 (m, 2H), 1.88 (m, 2H), 1.97 (m, 2H), 2.05 (s, 3H), 2.15 (s, 3H), 2.23 (m, 2H), 3.5 (m, 4H), 5.7 (m, 4H), 4.77 (m, 1H), 6.28 (d, 1H), 6.89 (m, 1H), 7.1 (m, 1H), 7.21 (m, 1H), 7.24 (s, 1H), 7.47 (m, 1H), 7.9 (m, 1H), 7.98 (d, 1H), 8.25 (m, 1H), 8.9 (s, 1H), 10.24 (s, 1H); Mass Spectrum: M+H⁺ 504.

EXAMPLE 9

Using an analogous procedure to that described in Example 8, the appropriate chloro-substituted pyrimidine was reacted with the appropriate alcohol to give the compounds described in the following table. Unless otherwise stated, each alcohol starting material is either commercially available or is readily prepared by standard methods from known materials.

TABLE III

[Structure: a benzamide with Me and HN-(pyrimidine bearing (R¹)ₘ) substituents on one phenyl ring, connected via C(O)NH to a pyridine bearing R⁴]

| No. | (R¹)ₘ | R⁴ | Note |
|---|---|---|---|
| 1 | 2-(3-dimethylaminopropoxy) | morpholino | (a) |
| 2 | 2-(2-dimethylaminopropoxy) | morpholino | (b) |
| 3 | 2-(3-dimethylamino-2,2-dimethylpropoxy) | morpholino | (c) |
| 4 | 2-[2-N-methylpyrrolidin-2-yl)ethoxy] | morpholino | (d) |
| 5 | 2-(N-isopropylpyrrolidin-3-yloxy) | morpholino | (e) |
| 6 | 2-(N-tert-butoxycarbonylpipendin-4-yloxy) | morpholino | (f) |
| 7 | 2-(N-methylpyrrolidin-2-ylmethoxy) | morpholino | (g) |
| 8 | 2-(N-methylpiperidin-3-ylmethoxy) | morpholino | (h) |
| 9 | 2-(N,N'-dimethylpiperazin-2-ylmethoxy) | morpholino | (i) |
| 10 | 2-(N-propylpiperidin-4-yloxy) | morpholino | (j) |

Notes (a) The product gave the following data: NMR Spectrum: (DMSOd₆) 1.74 (m, 2H), 2.07 (s, 6H), 2.17 (s, 3H), 2.25 (t, 2H), 3.51 (m, 4H), 3.7 (m, 4H), 4.17 (t, 2H), 6.26 (d, 1H), 7.1 (m, 1H), 7.24 (s, 1H), 7.25 (m, 1H), 7.6 (m, 1H), 7.88 (m, 1H), 8.0 (d, 1H), 8.27 (m, 1H), 8.97 (s, 1H), 10.28 (s, 1H); Mass Spectrum: M+H⁺ 492.

(b) The product gave the following data: NMR Spectrum: (DMSOd₆) 0.91 (d, 3H), 2.13 (s, 6H), 2.18 (s, 3H), 2.81 (m, 1H), 3.5 (m, 4H), 3.7 (m, 4H), 4.0 (m, 1H), 4.2 (m, 1H), 6.27 (d, 1H), 7.19 (m, 1H), 7.21 (s, 1H), 7.23 (m, 1H), 7.58 (m, 1H), 7.89 (m, 1H), 8.0 (d, 1H), 8.27 (m, 1H), 8.99 (s, 1H), 10.28 (s, 1H); Mass Spectrum: M+H⁺ 492.

(c) The product gave the following data: NMR Spectrum: (DMSOd₆) 0.88 (s, 6H), 2.15 (s, 6H), 1.18 (s, 3H), 3.34 (s, 2H), 3.52 (m, 4H), 3.71 (m, 4H), 3.94 (s, 2H), 6.23 (d, 1H), 7.1 (m, 1H), 7.22 (s, 1H), 7.24 (m, 1H), 7.49 (m, 1H), 7.91 (m, 1H), 8.0 (d, 1H), 8.28 (m, 1H), 9.01 (s, 1H), 10.29 (s, 1H); Mass Spectrum: M+H⁺ 520.

(d) The product gave the following data: NMR Spectrum: (DMSOd₆) 1.37 (m, 1H), 1.52 (m, 1H), 1.79 (m, 1H), 1.91–2.28 (m, 4H), 2.13 (s, 3H), 2.18 (s, 3H), 2.7 (m, 1H), 2.86 (m, 1H), 3.5 (m, 4H), 3.7 (m, 4H), 4.17 (m, 1H), 6.29 (d, 1H), 71 (m, 1H), 7.21 (s, 1H), 7.23 (m, 1H), 7.49 (m, 1H), 7.91 (m, 1H), 8.0 (d, 1H), 8.27 (m, 1H), 8.98 (s, 1H), 10.27 (s, 1H); Mass Spectrum: M+H⁺ 518.

(e) The product gave the following data: NMR Spectrum: (DMSOd₆) 0.93 (s, 3H), 0.97 (s, 3H), 1.8 (m, 1H), 2.05–2.36 (m, 3H), 2.17 (s, 3H), 2.55 (m, 1H), 2.65 (m, 1H), 2.75 (m, 1H), 3.5 (m, 4H), 3.7 (m, 4H), 5.08 (m, 1H), 6.3 (d, 1H), 7.1 (m, 1H), 7.21 (s, 1H), 7.23 (m, 1H), 7.5 (m, 1H), 7.85 (m, 1H), 7.99 (d, 1H), 8.27 (m, 1H), 8.97 (s, 1H), 10.28 (s, 1H); Mass Spectrum: M+H⁺ 518.

(f) The product gave the following data: NMR Spectrum: (DMSOd₆) 1.47 (s, 9H), 1.58–1.8 (m, 4H), 1.98 (m, 2H), 2.04 (m, 3H), 3.06 (m, 2H), 3.58 (m, 4H), 3.81 (m, 4H), 5.15 (m, 1H), 6.25 (d, 1H), 6.68 (s, 1H), 6.9 (s, 1H), 7.11 (s, 1H), 7.26 (m, 2H), 7.83 (m, 1H), 7.92 (m, 1H), 8.07 (m, 1H), 8.3 (m, 1H); Mass Spectrum: M+H⁺ 590.

The N-tert-butoxycarbonyl-4-hydroxypiperidine used as a starting material was obtained from a commercial source, for example from Neosystem, F67100, Strasbourg, France, or was prepared by the following procedure. A solution of di-tert-butyl dicarbonate (53.9 g) in methylene chloride (100 ml) was added dropwise to a stirred mixture of 4-hydroxypiperidine (25 g), triethylamine (50 ml) and methylene chloride (250 ml) which had been cooled to 0° C. The resultant mixture was allowed to warm to ambient temperature and was stirred for 18 hours. The mixture was evaporated and the residue was purified by chromatography on silica a 2:1 mixture of isohexane and ethyl acetate as eluent. The oil so obtained was dried under vacuum at 60° C. to give N-tert-butoxycarbonyl-4-hydroxypiperidine as a white solid (49.1 g); NMR Spectrum: (DMSOd₆) 1.39 (s, 9H), 1.55 (m, 2H), 1.78 (m, 2H), 2.95 (m, 2H), 3.76 (m, 2H).

(g) The product gave the following data: NMR Spectrum: (DMSOd₆) 1.47–1.63 (m, 3H), 1.85 (m, 1H), 2.1 (m, 2H), 2.16 (s, 3H), 2.25 (s, 3H), 2.86 (m, 1H), 3.51 (m, 4H), 3.71 (m, 4H), 3.99 (m, 1H), 4.17 (m, 1H), 6.25 (d, 1H), 7.09 (m, 1H), 7.21 (s, 1H), 7.23 (m, 1H), 7.49 (m, 1H), 7.67 (m, 1H), 8.0 (d, 1H), 8.27 (m, 1H), 9.0 (s, 1H), 10.28 (s, 1H); Mass Spectrum: M+H⁺ 504.

(h) The product gave the following data: NMR Spectrum: (DMSOd₆) 0.92 (m, 1H), 1.4 (m, 1H), 1.6 (m, 3H), 1.79 (t, 1H), 1.9 (m, 1H), 2.08 (s, 3H), 2.18 (s, 3H), 2.69 (m, 1H), 3.35 (m, 1H), 3.52 (m, 4H), 3.7 (m, 4H), 4.03 (m, 2H), 6.27 (d, 1H), 7.10 (m, 1H), 7.20 (s, 1H), 7.22 (m, 1H), 7.47 (m, 1H), 7.92 (m, 1H), 8.0 (d, 1H), 8.27 (m, 1H), 8.99 (s, 1H), 10.28 (s, 1H); Mass Spectrum: M+H⁺ 518.

(i) The product gave the following data: NMR Spectrum: (DMSOd₆) 1.09 (t, 1H), 1.81 (t, 1H), 1.98 (t, 1H), 2.08 (s, 3H), 2.17 (s, 3H), 2.19 (s, 3H), 2.29 (m, 1H), 2.61 (m, 3H), 3.52 (m, 4H), 3.71 (m, 4H), 4.05 (m, 1H), 4.3 (m, 1H), 6.27 (d, 1H), 7.1 (m, 1H), 7.21 (s, 1H), 7.23 (m, 1H), 7.5 (m, 1H), 7.9 (m, 1H), 8.0 (d, 1H), 8.27 (m, 1H), 9.0 (s, 1H), 10.28 (s, 1H); Mass Spectrum: M+H⁺ 533.

(j) The reaction mixture was heated to 140° C. for 4 hours. The mixture was evaporated and the residue was purified by column chromatography on silica using increasingly polar mixtures of methylene chloride and methanol as eluent. The material so obtained was triturated under diethyl ether. The product so obtained gave the following data: NMR Spectrum: (DMSOd₆) 0.76 (t, 3H), 1.3 (m, 2H), 1.53 (m, 2H), 1.92 (m, 4H), 2.06 (m, 2H), 2.17 (s, 3H), 2.63 (m, 2H), 3.51 (m, 4H), 3.69 (m, 4H), 4.76 (m, 1H), 6.27 (d, 1H), 7.11 (d, 1H), 7.22 (m, 2H), 7.45 (m, 1H), 7.94 (d, 1H), 7.98 (d, 1H), 8.26 (d, 1H), 8.91 (s, 1H), 10.21 (s, 1H); Mass Spectrum: M+H⁺ 532.

The 4-hydroxy-N-propylpiperidine used as a starting material was obtained as follows:—

1-Iodopropane (22 ml) was added dropwise during 15 minutes to a stirred suspension of 4-hydroxypiperidine (20 g) in acetone (250 ml) and the resultant mixture was stirred at ambient temperature for 20 hours. The mixture was evaporated and the residue was partitioned between diethyl ether and 2N aqueous sodium hydroxide solution. The organic phase was washed with brine, dried over magnesium sulphate and evaporated to give 4-hydroxy-N-propylpiperidine as an oil (19.6 g); NMR Spectrum: (DMSOd₆) 0.82 (t, 3H), 1.16 (m, 4H), 1.66 (m, 2H), 1.91 (m, 2H), 2.06 (t, 2H), 2.64 (m, 2H), 3.38 (m, 1H), 4.45 (d, 1H); Mass Spectrum: M+H⁺ 144.

EXAMPLE 10

Using an analogous procedure to that described in Example 5, the appropriate chloro-substituted pyrimidine was reacted with the appropriate amine to give the compounds described in the following table. Unless otherwise stated, each amine starting material is either commercially available or is readily prepared by standard methods from known materials.

TABLE IV

[Structure: Me-substituted phenyl with HN-(pyrimidine with (R¹)ₘ at positions 2,5) and N-H linked to C(=O)-pyridine with R⁴]

| No. | (R¹)ₘ | R⁴ | Note |
|---|---|---|---|
| 1 | 2-morpholino | morpholino | (a) |
| 2 | 2-(2,6-dimethylmorpholin-4-yl) | morpholino | (b) |
| 3 | 2-(tetrahydro-4H-1,4-thiazin-4-yl) | morpholino | (c) |
| 4 | 2-(4-methylpiperazin-1-yl) | morpholino | (d) |
| 5 | 2-(4-isopropylpiperazin-1-yl) | morpholino | (e) |
| 6 | 2-(4-tert-butoxycarbonylpiperazin-1-yl) | morpholino | (f) |
| 7 | 2-(4-hydroxypiperidin-1-yl) | morpholino | (g) |
| 8 | 2-[N-(N-methylpiperidin-4-yl)amino] | morpholino | (h) |
| 9 | 2-[N-methyl-N-(N-methylpiperidin-4-yl)amino] | morpholino | (i) |
| 10 | 2-[N-(N-ethylpiperidin-3-yl)amino] | morpholino | (j) |
| 11 | 2-[N-(N-ethylpyrrolidin-2-ylmethyl)amino] | morpholino | (k) |
| 12 | 2-[2-(2-ethylimidazol-1-yl)ethylamino] | morpholino | (l) |
| 13 | 2-[2-(2-oxoimidazolidin-1-yl)ethylamino] | morpholino | (m) |
| 14 | 2-(2-imidazol-1-ylethylamino) | morpholino | (n) |
| 15 | 2-[3-(1,2,4-triazol-1-yl)propylamino] | morpholino | (o) |
| 16 | 2-(3-pyrrolidin-1-ylpropylamino) | morpholino | (p) |
| 17 | 2-[3-(2-oxopyrrolidin-1-yl)propylamino] | morpholino | (q) |
| 18 | 2-[2-(N-methylpyrrolidin-2-yl)ethylamino] | morpholino | (r) |
| 19 | 2-(3-imidazol-1-ylpropylamino) | morpholino | (s) |
| 20 | 2-(3-morpholinopropylamino) | morpholino | (t) |
| 21 | 2-(3-diethylaminopropylamino) | morpholino | (u) |
| 22 | 2-(3-dimethylamino-2,2-dimethylpropylamino) | morpholino | (v) |
| 23 | 2-(3-amino-2-hydroxypropylamino) | morpholino | (w) |
| 24 | 2-(4-dimethylaminobutylamino) | morpholino | (x) |
| 25 | 2-(4-imidazol-1-ylbutylamino) | morpholino | (y) |
| 26 | 6-[N-methyl-N-(N-methylpiperidin-4-yl)amino] | morpholino | (z) |
| 27 | 6-[N-(N-ethylpiperidin-3-yl)amino] | morpholino | (aa) |
| 28 | 6-(3-imidazol-1-ylpropylamino) | morpholino | (bb) |
| 29 | 6-[3-(4-methylpiperazin-1-yl)propylamino] | morpholino | (cc) |
| 30 | 6-[N-methyl-N-(3-morpholinopropyl)amino] | morpholino | (dd) |
| 31 | 6-(3-pyrrolidin-1-ylpropylamino) | morpholino | (ee) |
| 32 | 6-(4-dimethylaminobutylamino) | morpholino | (ff) |
| 33 | 6-(3-dimethylamino-2,2-dimethylpropylamino) | morpholino | (gg) |
| 34 | 6-(3-diethylaminopropylamino) | morpholino | (hh) |
| 35 | 6-(3-dimethylaminopropylamino) | morpholino | (ii) |
| 36 | 6-[3-(2-oxopyrrolidin-1-yl)propylamino] | morpholino | (jj) |

Notes (a) The product gave the following data: Mass Spectrum: M+H⁺ 476.

(b) The product gave the following data: Mass Spectrum: M+H⁺ 504.

(c) The product gave the following data: Mass Spectrum: M+H⁺ 492.

(d) The product gave the following data: NMR Spectrum: (DMSOd₆) 2.13 (s, 3H), 2.16 (s, 3H), 2.27 (m, 4H), 3.52 (m, 4H), 3.62 (m, 4H), 3.72 (m, 4H), 5.92 (m, 1H), 7.08 (m, 1H), 7.18 (m, 1H), 7.2 (m, 1H), 7.36 (m, 1H), 7.87 (m, 1H), 8.02 (m, 1H), 8.27 (m, 1H), 8.47 (s, 1H) 0.19 (s, 1H); Mass Spectrum: M+H⁺ 489.

(e) The product gave the following data: Mass Spectrum: M+H⁺ 517.

(f) The product gave the following data: Mass Spectrum: M+H⁺ 575.

(g) The product gave the following data: Mass Spectrum: M+H⁺ 490.

(h) The product gave the following data: NMR Spectrum: (DMSOd₆) 1.29 (m, 2H), 1.93 (m, 2H), 2.27 (s, 3H), 2.57 (m, 3H), 2.6 (m, 1H), 2.94 (t, 2H), 3.58 (m, 4H), 5.88 (m, 4H), 4.64 (m, 2H), 5.88 (m, 1H), 6.28 (m, 1H), 6.89 (m, 1H), 7.1 (s, 1H), 7.21 (m, 1H), 7.27 (s, 1H), 7.33 (m, 1H), 7.8 (s, 1H), 7.93 (m. 1H), 7.98 (m, 1H), 8.29 (m, 1H); Mass Spectrum: M+H⁺ 503.

(i) The product gave the following data: NMR Spectrum: (DMSOd₆) 1.68 (m, 2H), 1.88 (m, 2H), 2.09 (m, 2H), 2.27 (s, 3H), 2.28 (s, 3H), 2.91 (m, 2H), 3.03 (s, 3H), 3.6 (m, 4H), 3.82 (m, 4H), 4.6 (m, 1H), 5.89 (d, 1H), 6.25 (s, 1H), 6.9 (d, 1H), 7.1 (s, 1H), 7.24 (m, 1H), 7.32 (m, 1H), 7.85 (m, 1H), 8.0 (d, 1H), 8.3 (d, 1H); Mass Spectrum: M+H⁺ 517.

(j) The product gave the following data: NMR Spectrum: (DMSOd₆) 0.96 (t, 3H), 1.4 (m, 2H), 1.6 (m, 2H), 1.88 (m, 2H), 2.28 (s, 3H), 2.3 (m, 4H), 3.58 (m, 4H), 5.82 (m, 4H), 4.03 (m, 1H), 5.11 (m, 1H), 5.92 (m, 1H), 6.3 (s, 1H), 6.94 (m, 1H), 7.1 (s, 1H), 7.2 (m, 1H), 7.28 (s, 1H), 7.6 (m, 1H), 7.93 (m, 1H), 8.28 (m, 1H), 8.54 (m, 1H); Mass Spectrum: M+H⁺ 517.

(k) The product gave the following data: Mass Spectrum: M+H⁺ 517.

(l) The 2-(2-ethylimidazol-1-yl)ethylamine, used as a starting material, is disclosed in Chemical Abstracts, volume 108, abstract 151535. The product gave the following data: Mass Spectrum: M+H⁺ 528.

(m) The product gave the following data: Mass Spectrum: M+H⁺ 518.

(n) The 2-imidazol-1-ylethylamine, used as a starting material, is disclosed in *J. Medicinal Chemistry*, 1986, 29, 523–530. The product gave the following data: Mass Spectrum: M+H⁺ 500.

(O) The 3-(1,2,4-triazol-1-yl)propylamine, used as a starting material, is disclosed in *J. Medicinal Chemistry*, 1986, 29, 523–530. The product gave the following data: Mass Spectrum: M+H⁺ 515.

(p) The product gave the following data: NMR Spectrum: (DMSOd₆) 1.59 (m, 6H), 2.18 (s, 3H), 2.3 (m, 6H), 3.19 (m, 2H), 3.51 (m, 4H), 3.71 (m, 4H), 5.87 (m, 1H), 7.09 (m, 1H), 7.18 (m, 1H), 7.22 (m, 1H), 7.43 (m, 1H), 7.77 (m, 1H), 7.92 (m, 1H), 8.26 (m, 1H), 8.31 (s, 1H), 10.17 (s, 1H); Mass Spectrum: M+H⁺ 517.

(q) The product gave the following data: Mass Spectrum: M+H⁺ 531.

(r) The product gave the following data: Mass Spectrum: M+H⁺ 517.

(s) The product gave the following data: Mass Spectrum: M+H⁺ 514.

(t) The product gave the following data: Mass Spectrum: M+H⁺ 533.

(u) The product gave the following data: Mass Spectrum: M+H⁺ 519.

(v) The product gave the following data: Mass Spectrum: M+H⁺ 519.

(w) The product gave the following data: NMR Spectrum: (DMSOd₆) 2.57 (s, 3H), 2.28 (m, 2H), 2.23 (m, 2H), 3.52 (m, 4H), 3.72 (m, 4H), 5.86 (m, 1H), 6.32 (m, 1H), 7.08 (m, 1H), 7.18 (m, 1H), 7.21 (m, 1H), 7.47 (m, 1H), 7.79 (m, 1H), 7.85 (m, 1H), 8.27 (m, 1H), 8.41 (s, 1H), 10.17 (s, 1H); Mass Spectrum: M+H⁺ 479.

(x) The product gave the following data: NMR Spectrum: (DMSOd₆) 2.57 (s, 3H), 2.28 (m, 2H), 2.23 (m, 2H), 3.52

(m, 4H), 3.72 (m, 4H), 5.86 (m, 1H), 6.32 (m, 1H), 7.08 (m, 1H), 7.18 (m, 1H), 7.21 (m, 1H), 7.47 (m, 1H), 7.79 (m, 1H), 7.85 (m, 1H), 8.27 (m, 1H), 8.41 (s, 1H), 10.17 (s, 1H); Mass Spectrum: M+H$^+$ 505.

(y) The 4-imidazol-1-ylbutylamine, used as a starting material, is disclosed in J. Medicinal Chemistry, 1987, 30, 185–193. The product gave the following data: Mass Spectrum: M+H$^+$ 528.

(z) The product gave the following data: NMR Spectrum: (DMSOd$_6$) 1.66 (m, 2H), 2.86 (m, 4H), 2.12 (m, 2H), 2.26 (s, 3H), 2.28 (s, 3H), 2.83 (s, 3H), 2.9 (m, 2H), 3.57 (m, 4H), 3.82 (m, 4H), 5.79 (s, 1H), 6.38 (s, 1H), 6.89 (m, 1H), 7.07 (m, 1H), 7.14 (m, 1H), 7.22 (m, 1H), 7.92 (m, 1H), 8.03 (s, 1H), 8.3 (m, 1H); Mass Spectrum: M+H$^+$ 517.

(aa) The product gave the following data: NMR Spectrum: (DMSOd$_6$) 1.06 (m, 3H), 1.52 (m, 2H), 1.72 (m, 4H), 2.26 (s, 3H), 2.28 (m, 6H), 2.59 (m, 1H), 3.58 (m, 4H), 3.83 (m, 4H), 5.58 (s, 1H), 6.3 (s, 1H), 6.92 (m, 1H), 7.1 (m, 1H), 7.22 (m, 1H), 7.33 (m, 1H), 7.78 (m, 1H), 7.88 (s, 1H), 8.18 (s, 1H), 8.31 (m, 1H); Mass Spectrum: M+H$^+$ 517.

(bb) The product gave the following data: Mass Spectrum: M+H $^+$ 514.

(cc) The product gave the following data: NMR Spectrum: (DMSOd$_6$) 1.61 (m, 2H), 2.12 (s, 3H), 2.17 (s, 3H), 2.28 (m, 5H), 3.13 (m, 2H), 3.52 (m, 4H), 3.72 (m, 4H), 5.46 (s, 1H), 6.78 (m, 1H), 7.1 (m, 1H), 7.19 (m, 1H), 7.23 (m, 1H), 7.5 (m, 1H), 7.74 (m, 114), 7.98 (m, 1H), 8.2 (m, 1H), 8.27 (m, 1H), 10.25 (s, 1H); Mass Spectrum: M+H$^+$ 546.

(dd) The product gave the following data: Mass Spectrum: M+H$^+$ 547.

The N-(3-methylaminopropyl)morpholine, used as a starting material, was obtained by bubbling methylamine gas for 10 minutes through a solution of 3-morpholinopropyl chloride (3.27 g) in ethanol (30 ml). The resultant mixture was allowed to stand for 1 hour and then evaporated. The residual oil was triturated under diethyl ether and the resultant solid was dried under vacuum. There was thus obtained the required starting material (1.58 g).

(ee) The product gave the following data: NMR Spectrum: (DMSOd$_6$) 1.62 (m, 6H), 2.15 (s, 3H), 2.36 (m, 6H), 3.14 (m, 2H), 3.52 (m, 4H), 3.72 (m, 4H), 6.72 (m, 1H), 7.08 (m, 1H), 7.2 (m, 1H), 7.22 (s, 1H), 7.48 (m, 1H), 7.76 (m, 1H), 7.96 (s, 1H), 8.17 (s, 1H), 8.26 (m, 1H), Mass Spectrum: M+H$^+$ 517.

(ff) The product gave the following data: Mass Spectrum: M+H$^+$ 505.

(gg) The product gave the following data: Mass Spectrum: M+H$^+$ 519.

(hh) The product gave the following data: Mass Spectrum: M+H$^+$ 519.

(ii) The product gave the following data: NMR Spectrum: (DMSOd$_6$) 1.56 (m, 2H), 2.09 (s, 6H), 2.17 (s, 3H), 3.14 (m, 2H), 3.5 (m, 4H), 3.7 (m, 4H), 5.46 (s, 1H), 6.75 (m, 1H), 7.08 (m, 1H), 7.2 (m, 1H), 7.23 (m, 1H), 7.5 (m, 1H), 7.75 (m, 1H), 7.98 (m, 1H), 8.2 (m, 1H), 8.24 (m, 1H), 10.24 (s, 1H); Mass Spectrum: M+H$^+$ 491.

(jj) The product gave the following data: NMR Spectrum: (DMSOd$_6$) 1.63 (t, 2H), 1.87 (t, 2H), 2.16 (s, 3H), 3.19 (t, 4H), 3.3 (t, 4H), 3.51 (m, 4H), 3.7 (m, 4H), 5.47 (s, 1H), 6.74 (m, 1H), 7.1 (m, 1H), 7.2 (m, 1H), 7.22 (s, 1H), 7.5 (m, 1H), 7.73 (m, 1H), 7.98 (s, 1H), 8.26 (m, 2H), 10.24 (s, 1H); Mass Spectrum: M+H$^+$ 531.

EXAMPLE 11

4-[2-Methyl-5-(2-morpholinopyrid-4-ylcarbonylamino) anilino]-2-(piperidin-4-yloxy)pyrimidine Trifluoroacetic acid (5 ml) was added to a solution of 2(1-tert-butoxycarbonylpiperidin-4-yloxy)-4-[2-methyl-5-(2-morpholinopyrid-4-ylcarbonylamino)anilino]pyrimidine (0.212 g) in methylene chloride (5 ml) and the resultant mixture was stirred at ambient temperature for 2 hours. The mixture was evaporated and the residue was partitioned between methylene chloride and water. The aqueous phase was passed through an ion exchange column (isolute SCX column from International Sorbent Technology Limited, Hengoed, Mid-Glamorgan, UK) using a 99:1 mixture of methanol and a saturated aqueous ammonium hydroxide solution as eluent. The product so obtained was triturated under diethyl ether and there was thus obtained the title compound as a solid (0.065 g); NMR Spectrum: (DMSOd$_6$) 1.2 (m, 2H), 1.87 (m, 2H), 2.17 (s, 3H), 2.19 (s, 3H), 2.27 (m, 2H), 2.95 (m, 2H), 3.5 (m, 4H), 3.7 (m, 4H), 4.85 (m, 1H), 6.27 (d, 1H), 7.1 (m, 1H), 7.21 (s, 1H), 7.23 (m, 1H), 7.5 (m, 1H), 7.9 (m, 1H), 8.0 (d, 1H), 8.27 (m, 1H), 9.0 (s, 1H), 10.28 (s, 1H); Mass Spectrum: M+H$^+$ 490.

EXAMPLE 12

4-[2-Methyl-5-(2-morpholinopyrid-4-ylcarbonylamino) anilino]-2-(piperazin-1-yloxy)pyrimidine trihydrochloride A mixture of 2-(4-tert-butoxycarbonylpiperazin-1-yl)$_4$-[2-methyl-5-(2-morpholinopyrid-4-ylcarbonylamino) anilino]pyrimidine (0.184 g) and a saturated solution of hydrogen chloride in ethyl acetate (20 ml) was stirred at ambient temperature for 2 hours. The resultant precipitate was collected and washed with diethyl ether. There was thus obtained the title compound (0.248 g); NMR Spectrum: (DMSOd$_6$) 2.22 (s, 3H), 3.2 (m, 4H), 3.65 (m, 4H), 3.72 (m, 4H), 3.95 (m, 4H), 7.2 (d, 1H), 7.28 (d, 1H), 7.49 (m, 1H), 7.58 (s, 1H), 7.9 (d, 1H), 8.14 (m, 1H), 8.2 (d, 1H), 9.5 (m, 1H), 10.5 (s, 1H), 10.75 (s, 1H); Mass Spectrum: M+H$^+$ 475.

EXAMPLE 13

2-Allylamino-4-[2-methyl-5-(2-morpholinopyrid-4-ylcarbonylamino)anilino]pyrimidine A mixture of 2-chloro-4-[2-methyl-5-(2-morpholinopyrid-4-ylcarbonylamino)anilino]pyrimidine (0.2 g) and allylamine (0.4 ml) was stirred and heated to reflux for 18 hours. The mixture was evaporated and the residue was purified by column chromatography on silica using a 9:1 mixture of methylene chloride and methanol as eluent. There was thus obtained the title compound as a solid (0.135 g); NMR Spectrum: (DMSOd$_6$) 2.17 (s, 3H), 3.5 (m, 4H), 3.7 (m, 4H), 3.82 (m, 2H), 4.95 (m, 1H), 5.05 (m, 1H), 5.85 (m, 2H), 6.57 (br m, 1H), 7.07 (m, 1H), 7.17 (m, 2H), 7.43 (m, 1H), 7.78 (m, 1H), 7.87 (br m, 1H), 8.24 (m, 1H), 8.37 (s, 1H), 10.18 (s, 1H); Mass Spectrum: M+H$^+$ 446.

EXAMPLE 14

2-(N-Allyl-N-methylamino)-4-[2-methyl-5-(2-morpholinopyrid-4-ylcarbonylamino)anilino]pyrimidine A mixture of 2-chloro-4-[2-methyl-5-(2-morpholinopyrid-4-ylcarbonylamino)anilino]pyrimidine (0.2 g) and N-allyl-N-methylamine (0.25 ml) was stirred and heated to 75° C. for 3 hours. The mixture was cooled to ambient temperature and purified by column chromatography on silica using a 9:1 mixture of methylene chloride and methanol as eluent. The resultant oil was triturated under a mixture of isohexane and diethyl ether. There was thus obtained the title compound as a solid (0.055 g); NMR Spectrum: (DMSOd$_6$) 2.17 (s, 3H), 2.95 (s, 3H), 3.5 (m, 4H), 3.7 (m, 4H), 4.1 (d, 2H), 5.04 (m, 2H), 5.75 (m, 1H), 5.91 (m, 1H), 7.07 (m, 1H), 7.17 (m, 2H), 7.19 (m, 1H), 7.86 (m, 1H), 7.98 (m, 1H), 8.25 (m, 1H), 8.42 (s, 1H), 10.17 (s, 1H); Mass Spectrum: M+H$^+$ 460.

EXAMPLE 15

2-Isopropylamino-4-[2-methyl-5-(2-morpholinopyrid-4-ylcarbonylamino)anilino]pyrimidine A mixture of 2-chloro-4-[2-methyl-5-(2-morpholinopyrid-4-ylcarbonylamino)anilino]pyrimidine (0.2 g) and isopropylamine (5 ml) was heated to 100° C. in a sealed tube for 24 hours. The mixture was evaporated and the residue was partitioned between methylene chloride and water. The organic phase was washed with brine, dried over sodium sulphate and evaporated. The resultant solid was recrystallised from tert-butyl methyl ether to give the title compound (0.145 g); NMR Spectrum: (DMSOd$_6$) 1.04 (s, 3H), 1.06 (s, 3H), 2.17 (s, 3H), 3.5 (m, 4H), 3.7 (m, 4H), 3.97 (m, 1H), 5.82 (m, 1H), 6.2 (br m, 1H), 7.07 (m, 1H), 7.19 (m, 2H), 7.45 (m, 1H), 7.78 (m, 1H), 7.87 (br m, 1H), 8.25 (m, 1H), 8.31 (s, 1H), 10.18 (s, 1H); Mass Spectrum: M+H$^+$ 448.

EXAMPLE 16

2-Amino-4-[2-methyl-5-(2-morpholinopyrid-4-ylcarbonylamino)anilino]pyrimidine

A mixture of 2-allylamino-4-[2-methyl-5-(2-morpholinopyrid-4-ylcarbonylamino)anilino]pyrimidine (0.151 g), methanesulphonic acid (0.1 ml) and 30% palladium-on-carbon (0.034 g) in DMA (1 ml) was stirred and heated to 140° C. for 24 hours. The mixture was cooled to ambient temperature and filtered. A mixture of methylene chloride and isohexane was added to the filtrate. The resultant precipitate was isolated and purified by column chromatography on silica using a 89:10:1 mixture of methylene chloride, methanol and a saturated aqueous ammonium hydroxide solution as eluent. There was thus obtained the title compound as a solid (0.01 g); NMR Spectrum: (DMSOd$_6$) 2.16 (s, 3H), 3.47 (m, 4H), 3.7 (m, 4H), 4.78 (br m, 4H), 5.98 (m, 1H), 7.01 (m, 1H), 7.16 (m, 2H), 7.39 (m, 1H), 7.65 (m, 1H), 7.72 (m, 1H), 8.17 (m, 1H); Mass Spectrum: M+H$^+$ 406.

EXAMPLE 17

2-(3-Dimethylamino-2-hydroxypropylamino)-4-[2-methyl-5-(2-morpholinopyrid-4-ylcarbonylamino)anilino]pyrimidine Formaldehyde (40% solution in water, 0.2 ml) was added to a suspension of 2-(3-amino-2-hydroxypropylamino)-4-[2-methyl-5-(2-morpholinopyrid-4-ylcarbonylamino)anilino]pyrimidine (0.1 g) and sodium cyanoborohydride (0.04 g) in a 3:1 mixture of ethanol and water (16 ml). Acetic acid (0.5 ml) was added to take the pH to approximately 4. The mixture was stirred at ambient temperature for 3 hours. The ethanol was evaporated and a saturated aqueous sodium bicarbonate solution was added to the residue to bring the pH to 8. The mixture was partitioned between methylene chloride and water. The organic phase was washed with brine, dried over sodium sulphate and evaporated to give the title compound as a solid (0.073 g); NMR Spectrum: (DMSOd$_6$) 2.11 (s, 3H), 2.16 (s, 3H), 3.11 (m, 2H), 3.52 (m, 4H), 3.7 (m, 4H), 5.86 (m, 1H), 6.24 (m, 1H), 7.08 (m, 1H), 7.18 (m, 1H), 7.22 (m, 1H), 7.47 (m, 1H), 7.78 (m, 1H), 7.88 (m, 1H), 8.26 (m, 1H), 8.21 (s, 1H), 10.19 (s, 1H); Mass Spectrum: M+H$^+$ 507.

EXAMPLE 18

4-[5-(3-Fluoro-5-morpholinobenzamido)-2-methylanilino]-2-hydroxypyrimidine

A mixture of 2-chloro-4-[5-(3-fluoro-5-morpholinobenzamido)-2-methylanilino]pyrimidine (0.1 g) and formic acid (1.0 ml) was stirred and heated to 65° C. for 16 hours. The mixture was allowed to cool to ambient temperature and was poured into a dilute aqueous ammonium hydroxide solution. The resultant precipitate was isolated and washed with anhydrous diethyl ether. There was thus obtained the title compound (0.09 g); NMR Spectrum: (DMSOd$_6$) 2.14 (s, 3H), 3.2 (m, 4H), 3.73 (m, 4H), 5.70 (br m, 1H), 6.95 (m, 1H), 7.09 (m, 1H), 7.19 (m, 1H), 7.25 (s, 1H), 7.4 (m, 1H), 7.5 (m, 1H), 7.68 (m, 1H), 10.14 (s, 1H), 10.5 (broad s, 1H); Mass Spectrum: M+H$^+$ 424.

EXAMPLE 19

4-[5-(3-Fluoro-5-morpholinobenzamido)-2-methylanilino]-2-(2-furylmethoxy)pyrimidine A mixture of 2-chloro-4-[5-(3-fluoro-5-morpholinobenzamido)-2-methylanilino]pyrimidine (0.18 g), approximately one equivalent of 2-furylmethanol (0.043 g) and potassium tert-butoxide (1M in tert-butanol, 0.88 ml) was stirred and heated to 100° C. for 2 hours. The mixture was partitioned between methylene chloride and water and the organic phase was washed with brine, dried over sodium sulphate and evaporated. The residue was purified by column chromatography on silica using increasingly polar mixtures of methylene chloride and methanol as eluent followed by increasingly polar mixtures of methylene chloride and methanol containing 1% aqueous ammonium hydroxide solution. There was thus obtained the title compound as a solid (0.17 g); NMR Spectrum: (DMSOd$_6$) 2.17 (s, 3H), 3.2 (m, 4H), 3.73 (m, 4H), 5.01 (s, 2H), 6.29 (d, 1H), 6.42 (m, 2H), 6.97 (m, 1H), 7.1 (m, 1H), 7.24 (m, 2H), 7.49 (d, 1H), 7.63 (s, 1H), 7.87 (s, 1H), 8.03 (d, 1H), 9.03 (s, 1H), 10.14 (s, 1H); Mass Spectrum: M+H$^+$ 504.

EXAMPLE 20

2-(3-Furylmethoxy)-4-{5-[3-(3-furylmethoxy)-5-morpholinobenzamido]-2-methylanilino}pyrimidine A mixture of 2-chloro-4-[5-(3-fluoro-5-morpholinobenzamido)-2-methylanilino]pyrimidine (0.18 g), approximately 2.5 equivalents of 3-furylmethanol (0.098 g) and potassium tert-butoxide (1M in tert-butanol, 2.0 ml) was stirred and heated to 140° C. for 2 hours. The mixture was partitioned between methylene chloride and water and the organic phase was washed with brine, dried over sodium sulphate and evaporated. The residue was purified by column chromatography on silica using increasingly polar mixtures of methylene chloride and methanol as eluent followed by increasingly polar mixtures of methylene chloride and methanol containing 1% aqueous ammonium hydroxide solution. There was thus obtained the title compound as a solid (0.08 g); NMR Spectrum: (DMSOd$_6$) 2.15 (s, 3H), 3.16 (m, 4H), 3.74 (m, 4H), 4.99 (s, 2H), 5.1 (s, 2H), 6.27 (d, 1H), 6.49 (s, 1H), 6.56 (s, 1H), 6.7 (s, 1H), 7.01 (s, 1H), 7.06 (s, 1H), 7.22 (d, 1H), 7.5 (d, 1H), 7.59 (s, 1H), 7.64 (d, 1H), 7.78 (s, 1H), 7.88 (s, 1H), 8.02 (d, 1H), 9.0 (s, 1H), 10.04 (s, 1H); Mass Spectrum: M+H$^+$ 582.

EXAMPLE 21

Unless otherwise stated, using an analogous procedure to that described in either Example 19 or Example 20 as appropriate, the appropriate chloro-substituted pyrimidine was reacted with either approximately one equivalent or 2.5 equivalents of the appropriate alcohol to give the compounds described in the following table. Unless otherwise stated, each alcohol starting material is commercially available or is readily prepared by standard methods from known materials.

TABLE V (structure: phenyl ring with Me group, HN linker to pyrimidine bearing $(R^1)_m$ at position 5, and NHC(O)-phenyl bearing $(R^4)_p$)

| No. | $(R^1)_m$ | $(R^4)_p$ | Note |
|---|---|---|---|
| 1 | 2-(2-pyridylmethoxy) | 3-morpholino-5-(2-pyridylmethoxy) | (a) |
| 2 | 2-(3-pyridylmethoxy) | 3-morpholino-5-(3-pyridylmethoxy) | (b) |
| 3 | 2-(6-methylpyrid-2-ylmethoxy) | 3-(6-methylpyrid-2-ylmethoxy)-5-morpholino- | (c) |
| 4 | 2-(4-pyridylmethoxy) | 3-fluoro-5-morpholino | (d) |
| 5 | 2-(2-pyridylmethoxy) | 3-fluoro-5-morpholino | (e) |
| 6 | 2-(3-pyridylmethoxy) | 3-fluoro-5-morpholino | (f) |
| 7 | 2-(6-methylpyrid-2-ylmethoxy) | 3-fluoro-5-morpholino | (g) |
| 8 | 2-(5-chloro-1-methylimidazol-2-ylmethoxy) | 3-fluoro-5-morpholino | (h) |
| 9 | 2-(1-methylimidazol-2-ylmethoxy) | 3-fluoro-5-morpholino | (i) |
| 10 | 2-(2-thiazolylmethoxy) | 3-fluoro-5-morpholino | (j) |
| 11 | 2-(3-dimethylamino-2,2-dimethylpropoxy) | 3-fluoro-5-morpholino | (k) |
| 12 | 2-(N-methylpiperidin-4-yloxy) | 3-fluoro-5-morpholino | (l) |
| 13 | 2-(N-methylpiperidin-4-yloxy) | 3-(N-methylpiperidin-4-yloxy)-5-morpholino | (l) |
| 14 | 2-(N-propylpiperidin-4-yloxy) | 3-morpholino | (m) |

Notes (a) The product gave the following data: NMR Spectrum: (CDCl$_3$) 1.77 (s, 3H), 3.13 (m, 4H), 3.8 (m, 4H), 5.17 (s, 2H), 5.59 (s, 2H), 6.24 (d, 1H), 6.6 (s, 1H), 6.68 (s, 1H), 7.13 (m, 1H), 7.19 (m, 2H), 7.44 (d, 1H), 7.54 (d, 1H), 7.68 (m, 2H), 8.11 (m, 2H), 8.34 (d, 1H), 8.58 (d, 1H), 9.06 (s, 1H); Mass Spectrum: M+H$^+$ 604.

(b) The product gave the following data: NMR Spectrum: (CDCl$_3$) 2.16 (s, 3H), 3.17 (m, 4H), 3.74 (m, 4H), 5.19 (s, 2H), 5.31 (s, 2H), 6.3 (d, 1H), 6.78 (s, 1H), 7.04 (s, 1H), 7.08 (s, 1H), 7.24 (d, 1H), 7.43 (m, 1H), 7.49 (m, 1H), 7.77 (d, 1H), 7.9 (m, 2H), 8.49 (d, 1H), 8.55 (d, 1H), 8.61 (s, 1H), 8.69 (s, 1H), 9.07 (s, 1H), 10.09 (s, 1H); Mass Spectrum: M+H$^+$ 604.

(c) The product gave the following data: NMR Spectrum: (DMSOd$_6$) 2.14 (s, 3H), 2.21 (s, 3H), 3.15 (m, 4H), 3.62 (m, 4H), 5.15 (s, 2H), 5.27 (s, 2H), 6.27 (d, 1H), 6.79 (s, 1H), 7.02 (s, 1H), 7.08 (s, 1H), 7.13 (m, 2H), 7.17 (m, 2H), 7.31 (d, 1H), 7.51 (m, 1H), 7.62 (t, 1H), 7.7 (m, 1H), 7.83 (s, 1H), 8.01 (d, 1H), 9.03 (s, 1H), 10.04 (s, 1H); Mass Spectrum: M+H$^+$ 632.

The 6-methylpyrid-2-ylmethanol used as a starting material can be obtained using the procedure described in *Heterocycles*, 1986, 24, 2169–2172.

(d) The product gave the following data: NMR Spectrum: (DMSOd$_6$) 2.13 (s, 3H), 3.2 (m, 4H), 3.73 (m, 4H), 5.31 (s, 2H), 6.3 (d, 1H), 6.96 (d, 1H), 7.11 (d, 1H), 7.26 (m, 4H), 7.49 (d, 2H), 7.87 (s, 1H), 8.01 (d, 1H), 8.48 (m, 2H), 9.05 (s, I); Mass Spectrum: M+H$^{30}$ 515.

(e) The product gave the following data: NMR Spectrum: (DMSOd$_6$) 2.15 (s, 3H), 3.2 (m, 4H), 3.73 (m, 4H), 5.33 (s, 2H, 6.29 (d, 1H), 6.96 (m, 1H), 7.1 (m, 1H), 7.24 (m, 3H), 7.35 (d, 1H), 7.74 (m, 1H), 7.84 (m, 1H), 8.01 (d, 1H), 8.49 (d, 1H), 9.04 (s, 1H), 10.13 (s, 1H); Mass Spectrum: M+H$^+$ 515.

(f) The product gave the following data: NMR Spectrum: (DMSOd$_6$) 2.15 (s, 3H), 3.2 (m, 4H), 3.73 (m, 4H), 5.3 (s, 2H), 6.3 (d, 1H), 6.96 (m, 1H), 7.1 (m, 1H), 7.24 (m, 2H), 7.34 (m, 1H), 7.49 (m, 1H), 7.75 (d, 1H), 7.89 (s, 1H), 8.03 (d, 1H), 8.48 (m, 1H), 8.57 (s, 1H), 9.04 (s, 1H), 10.13 (s, 1H); Mass Spectrum: M+H$^+$ 515.

(g) The product gave the following data: NMR Spectrum: (DMSOd$_6$) 2.15 (s, 3H), 2.41 (s, 3H), 3.2 (m, 4H), 3.72 (m, 4H), 5.27 (s, 2H), 6.28 (d, 1H), 6.96 (m, 1H), 7.12 (m, 3H), 7.24 (m, 2H), 7.52 (m, 1H), 7.62 (t, 1H), 7.85 (d, 1H), 8.01 (d, 1H), 9.04 (s, 1H), 10.12 (s, 1H); Mass Spectrum: M+H$^+$ 529.

(h) The product gave the following data: NMR Spectrum: (DMSOd$_6$) 2.17 (s, 3H), 3.19 (m, 4H), 3.55 (s, 3H), 3.73 (m, 4H), 5.28 (s, 2H), 6.34 (d, 1H), 6.93 (s, 1H), 6.96 (m, 1H), 7.09 (m, 2H), 7.49 (m, 1H), 7.94 (m, 1H), 8.04 (d, 1H), 9.04 (s, 1H), 10.15 (s, 1H); Mass Spectrum: M+H$^+$ 552.

The 5-chloro-1-methylimidazol-2-ylmethanol used as a starting material can be obtained using the procedure described in *J. Chem. Soc.*, 1927, 3132.

(i) The product gave the following data: NMR Spectrum: (DMSOd$_6$) 2.18 (s, 3H), 3.17 (m, 4H), 3.64 (s, 3H), 3.73 (m, 4H), 5.29 (s, 2H), 6.34 (d, 1H), 6.78 (s, 1H), 6.95 (m, 1H), 7.08 (m, 2H), 7.12 (s, 1H), 7.22 (m, 2H), 7.97 (m, 1), 8.04 (d, 1H), 9.01 (s, 1H), 10.02 (s, 1H); Mass Spectrum: M+H$^+$ 518.

The 1-methylimidazol-2-ylmethanol used as a starting material can be obtained using the procedure described in *J. Chem. Soc.*, 1927, 3135.

(j) The product gave the following data: NMR Spectrum: (DMSOd$_6$) 2.16 (s, 3H), 3.2 (m, 4H), 3.73 (m, 4H), 5.56 (s, 2H), 6.32 (d, 1H), 6.96 (m, 1H), 7.1 (m, 2H), 7.23 (m, 2H), 7.51 (m, 1H), 7.69 (m, 1H), 7.97 (m, 1H), 7.76 (m, 1H), 7.86 (m, 1H), 8.04 (d, 1H), 9.12 (s, 1H), 10.13 (s, 1H); Mass Spectrum: M+H$^+$ 521.

The 2-thiazolylmethanol used as a starting material can be obtained using the procedure described in *J. Org. Chem.*, 1995, 60, 4749.

(k) Although an analogous procedure to that described in Example 20 was used involving 2.5 equivalents of 3-dimethylamino-2,2-dimethylpropanol and a reaction temperature of 140° C., only the 2-chloro group was displaced. The product gave the following data: NMR Spectrum: (DMSOd$_6$) 0.86 (s, 6H), 2.13 (s, 6H), 2.18 (s, 3H), 3.21 (m, 4H), 3.27 (s, 2H), 3.73 (s, 4H), 3.98 (s, 2H), 6.17 (d, 1H), 6.95 (m, 1H), 7.12 (m, 2H), 7.22 (m, 1H), 7.36 (m, 1H), 8.03 (s, 1H), 8.06 (d, 1H), 8.58 (s, 1H), 10.04 (s, 1H); Mass Spectrum: M+H$^+$ 537.

(l) Although a similar procedure to that described in Example 20 was used involving 4 equivalents of 4-hydroxy-N-methylpiperidine and a reaction temperature of 140° C. for 7 hours, the 3-fluoro group was only partially displaced. The reaction mixture was purified by column chromatography on silica using increasingly polar mixtures of methylene chloride and methanol as eluent followed by increasingly polar mixtures of methylene chloride and methanol containing 1% aqueous ammonium hydroxide solution. There were thus obtained in turn Compound No. 12; NMR Spectrum: (DMSOd$_6$) 1.57 (m, 2H), 1.82–2.06 (m, 4H), 2.04 (s, 3H), 2.17 (s, 3H), 2.48 (m, 1H), 3.17 (m, 1H) 3.21 (m, 4H), 3.73 (m, 4H), 4.77 (m, 1H), 6.27 (d, 1H), 6.96 (m, 1H), 7.13 (m, 1H), 7.2 (d, 1H), 7.27 (s, 1H), 7.46 (d, 1H), 7.9 (s, 1H), 7.99 (d, 1H), 8.9 (s, 1H), 10.11 (s, 1H); Mass Spectrum: M+H$^+$ 521; and Compound No. 13; NMR Spectrum: (DMSOd$_6$) 1.62 (m, 4H), 1.83–2.22 (m, 8H), 2.05 (s, 3H), 2.16 (s, 6H), 2.54

(n, 4H), 3.16 (m, 4H), 3.73 (m, 4H), 4.22 (m, 1H), 4.77 (m, 1H), 6.27 (d, 1H), 6.64 (s, 1H), 6.95 (s, 1H), 7.04 (s, 1H), 7.19 (d, 1H), 7.46 (d, 1H), 7.9 (s, 1H), 7.99 (d, 1H), 8.9 (s, 1H), 10.0 (s, 1H); Mass Spectrum: M+H$^+$ 615.

(m) An analogous procedure to that described in Example 20 was used involving 2.5 equivalents of 4-hydroxy-N-propylpiperidine and a reaction temperature of 140° C. The product gave the following data: NMR Spectrum: (DMSOd$_6$) 0.76 (t, 3H), 1.28 (m, 2H), 1.53 (m, 2H), 1.92 (m, 4H), 2.04 (m, 2H), 2.17 (s, 3H), 2.60 (m, 2H), 3.16 (m, 4H), 3.74 (m, 4H), 4.76 (m, 1H), 6.28 (d, 1H), 7.12 (d, 1H), 7.19 (d, 1H), 7.35 (m, 2H), 7.44 (m, 2H), 7.93 (s, 1H), 7.97 (d, 1H), 8.87 (s, 1H), 10.05 (s, 1H); Mass Spectrum: M+H$^+$ 531.

EXAMPLE 22

4-[2-Methyl-5-(3-morpholinobenzamido)anilino]-2-[2-(N-methylpyrrolidin-2-yl)ethylamino]pyrimidine A mixture of 2-chloro-4-[2-methyl-5-(3-morpholinobenzamido)anilino]pyrimidine (0.64 g), 2-(N-methylpyrrolidin-2-ylethylamine (0.44 ml), N,N-di-isopropylethylamine (0.52 ml) and n-butanol (7 ml) was stirred and heated to 100° C. for 18 hours. The mixture was evaporated and the residue was purified by column chromatography on silica using increasingly polar mixtures of methylene chloride and methanol as eluent followed by increasingly polar mixtures of methylene chloride and methanol containing 1% aqueous ammonium hydroxide solution. There was thus obtained the title compound as a solid (0.33 g); NMR Spectrum: (DMSOd$_6$) 1.44 (m, 2H), 1.62 (m, 2H), 1.88 (m, 2H), 2.15 (s, 3H), 2.31 (m, 4H), 3.04 (m, 2H), 3.17 (m, 5H), 3.74 (m, 4H), 5.88 (d, 1H), 6.5 (m, 1H), 7.13 (m, 2H), 7.34 (m, 2H), 7.44 (m, 2H), 7.77 (d, 1H), 7.9 (m, 1H), 8.37 (s, 1H), 10.04 (s, 1H); Mass Spectrum: M+H$^+$ 516.

EXAMPLE 23

4-[5-(3-Fluoro-5-morpholinobenzamido)-2-methylanilino]-2-morpholinopyrimidine

A mixture of 4-[5-(3-fluoro-5-morpholinobenzamido)-2-methylanilino]2-methylthiopyrimidine (0.228 g) and morpholine (1 ml) was stirred and heated to 150° C. for 10 days. The reaction mixture was allowed to cool to ambient temperature and poured into water (10 ml). The resultant precipitate was collected by filtration and dried in a vacuum oven at 60° C. for 16 hours. There was thus obtained the title compound (0.175 g); NMR Spectrum: (DMSOd$_6$) 2.18 (s, 3H), 3.21 (m, 4H), 3.59 (m, 8H), 3.74 (m, 4H), 5.98 (d, 1H), 6.96 (m, 1H), 7.09 (m, 1H), 7.18 (m, 1H), 7.26 (m, 1H), 7.38 (m, 1H), 7.89 (d, 1H), 8.01 (m, 1H), 8.49 (s, 1H), 10.07 (s, 1H); Mass Spectrum: M+H$^+$ 493.

EXAMPLE 24

2-Chloro-4-[5-(4-dibenzofuranylcarbonylamino)-2-methylanilino]pyrimidine

A mixture of N-(3-amino-4-methylphenyl)dibenzofuran-4-carboxamide (1.5 g), 2,4-dichloropyrimidine (1.4 g), N,N-di-isopropylethylamine (2.9 ml) and n-butanol (70 ml) was stirred and heated to 120° C. for 76 hours. The mixture was evaporated and the residue was purified by column chromatography on silica using increasingly polar mixtures of isohexane and ethyl acetate as eluent. The material so obtained was triturated under ethyl acetate. There was thus obtained the title compound (0.83 g); NMR Spectrum: (DMSOd$_6$) 2.17 (s, 3H), 6.53 (d, 1H), 7.31 (d, 1H), 7.43–7.65 (m, 4H), 7.79 (m, 2H), 7.84 (d, 1H), 8.1 (d, 1H), 8.21 (d, 1H), 8.34 (d, 1H), 9.62 (s, 1H), 10.42 (s, 1H); Mass Spectrum: M+H$^+$ 429 and 431.

The N-(3-amino-4-methylphenyl)dibenzofuran-4-carboxamide used as a starting material was obtained as follows:—

A solution of dibenzofuran-4-carbonyl chloride [22.5 g; prepared by the reaction of dibenzofuran-4-carboxylic acid (*J. Chem. Soc. Perkin I*, 1998, 457–465) and oxalyl chloride using a conventional procedure] in methylene chloride (150 ml) was added dropwise to a stirred mixture of 4-methyl-3-nitroaniline (13.5 g), triethylamine (24.8 ml) and methylene chloride (40 ml) which had been cooled to 0° C. The resultant mixture was stirred at ambient temperature for 18 hours. The mixture was evaporated and the residue was partitioned between methylene chloride and a saturated aqueous sodium bicarbonate solution. The organic phase was dried over magnesium sulphate and evaporated. The residue was triturated under isohexane and the resultant solid was isolated and dried under vacuum at 65° C. for 18 hours. There was thus obtained N-(4-methyl-3-nitrophenyl)dibenzofuran-4-carboxamide (30.6 g); NMR Spectrum: (DMSOd$_6$) 2.5 (s, 3H), 7.54 (m, 4H), 7.81 (m, 1H), 7.98 (m, 1H), 7.99 (m, 1H), 8.23 (m, 1H), 8.36 (m, 1H), 9.79 (m, 1H); Mass Spectrum: M+H$^+$ 347.

A mixture of N-(4-methyl-3-nitrophenyl)dibenzofuran-4-carboxamide (23.7 g) 10% palladium-on-carbon catalyst (2.5 g) and methanol (1 L) was stirred underan atmosphere pressure of hydrogen for 21 hours. Methylene chloride (500 ml) was added and the reaction mixture was filtered through diatomaceous earth. The filtrate was evaporated and the residue was stirred under a mixture of isohexane and ethyl acetate for 30 minutes. The resultant solid was isolated, washed with diethyl ether and dried under vacuum at 65° C. for 18 hours. There was thus obtained N-(3-amino-4-methylphenyl)dibenzofuran-4-carboxamide (31.1 g); NMR Spectrum: (DMSOd$_6$) 2.05 (s, 3H), 5.1 (s, 2H), 6.89 (m, 2H), 7.19 (d, 1H), 7.5 (m, 3H), 7.82 (m, 2H), 8.2 (m, 1H), 8.29 (m, 1H), 10.05 (s, 1H); Mass Spectrum: M+H$^+$ 317.

EXAMPLE 25

4-[5-(4-Dibenzofuranylcarbonylamino)-2-methylanilino]-2-(N-methylpiperidin-4-yloxy)pyrimidine Using an analogous procedure to that described in Example 8, 2-chloro-4-[5-(4-dibenzofuranylcarbonyl-amino)-2-methylanilino]pyrimidine was reacted with 4-hydroxy-N-methylpiperidine. The reaction mixture was evaporated and the residue was purified by column chromatography on silica using increasingly polar mixtures of methylene chloride and methanol as eluent followed by increasingly polar mixtures of methylene chloride and methanol containing 1% aqueous ammonium hydroxide solution. There was thus obtained the title compound; NMR Spectrum: (DMSOd$_6$) 1.56 (m, 2H), 1.84–2.1 (m, 4H), 1.97 (s, 3H), 2.17 (s, 3H), 2.53 (m, 2H), 4.78 (m, 1H), 6.22 (d, 1H), 7.18 (d, 1H), 7.38–7.58 (m, 4H), 7.77 (d, 1H), 7.86 (m, 2H), 7.93 (d, 1H), 8.19 (d, 1H), 8.28 (d, 1H); Mass Spectrum: M+H$^+$ 507.

EXAMPLE 26

4-[5-(4-Dibenzofuranylcarbonylamino)-2-methylanilino]-2-(3-dimethylamino-2,2-dimethylpropoxy)pyrimidine Using an analogous procedure to that described in Example 8, 2-chloro-4-[5-(4-dibenzofuranylcarbonyl-amino)-2-methylanilino]pyrimidine was reacted with 3-dimethylamino-2,2-dimethylpropanol. The reaction mixture was evaporated and the residue was purified by column chromatography on silica using increasingly polar mixtures of methylene chloride and methanol as eluent followed by increasingly polar mixtures of methylene chloride and methanol containing 1% aqueous ammonium hydroxide solution. There was thus obtained the title compound; NMR Spectrum: (DMSOd$_6$) 0.85 (s, 6H), 2.14 (s, 6H), 2.18 (s, 2H), 3.94 (s, 2H), 6.22 (d, 1H), 7.23 (d, 1H), 7.4–7.58 (m, 4H), 7.78 (d, 1H), 7.84 (d, 1H), 7.96 (m, 2H), 8.2 (d, 1H), 8.31 (d, 1H); Mass Spectrum: M+H$^+$ 524.

EXAMPLE 27

4-[5-(4-Dibenzofuranylcarbonylamino)-2-methylanilino]-2-methoxypyrimidine

A mixture of 2-chloro-4-[5-(4-dibenzofuranylcarbonylamino)-2-methylanilino]pyrimidine (0.1 g), methanol (2 ml) and a 2M solution of hydrogen chloride in diethyl ether (0.5 ml) was stirred and heated to 70° C. for 24 hours. The reaction was evaporated and the residue was purified by column chromatography on silica using a 9:1 mixture of methylene chloride and methanol as eluent. There was thus obtained the title compound as a solid (0.025 g); NMR Spectrum: (DMSOd$_6$) 2.26 (s, 3H), 3.85 (s, 3H), 6.36 (d, 1H), 7.34 (m, 1H), 7.46–7.7 (m, 4H), 7.87 (m, 1H), 7.92 (m, 1H), 8.01 (s, 1H), 8.09 (d, 1H), 8.29 (d, 1H), 8.4 (d, 1H), 9.09 (s, 1H), 10.46 (s, 1H); Mass Spectrum: M+H$^+$ 425.

EXAMPLE 28

4-[5-(3-Fluoro-5-morpholinobenzamido)-2-methylanilino]-2-methylsulphonylpyrimidine A mixture of 4-[5-(3-fluoro-5-morpholinobenzamido)-2-methylanilino]-2-methylthiopyrimidine (0.4 g), hydrogen peroxide (0.2 ml), sodium tungstate dihydrate (0.002 g) in DMA (2 ml) was stirred and heated to 95° C. for 18 hours. Second portions of hydrogen peroxide (0.05 ml) and sodium tungstate dihydrate (0.001 g) were added and the mixture was heated to 95° C. for a further 4 hours. Water (15 ml) was added and the resultant precipitate was isolated and washed in turn with water and diethyl ether. The solid so obtained was purified by column chromatography on silica using increasingly polar mixtures of methylene chloride and methanol as eluent. There was thus obtained the title compound (0.26 g); NMR Spectrum: (DMSOd$_6$) 2.17 (s, 3H), 3.22 (m, 4H), 3.73 (m, 4H), 6.71 (m, 1H), 6.96 (m, 1H), 7.19 (m, 1H), 7.26 (m, 2H), 7.54 (d, 1H), 7.83 (s, 1H), 8.34 (d, 1H), 9.83 (s, 1H), 10.18 (s, 1H); Mass Spectrum: M+H$^+$ 486.

EXAMPLE 29

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium | 1.5 |
| (e) | Injection 1 | (50 mg/ml) |
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP 2.26% | w/v |
| | Citric acid 0.38% | w/v |
| | Polyethylene glycol 400 3.5% | w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | mg/ml |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | mg/ml |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | mg/ml |
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |
| (l) | Ointment | ml |
| | Compound X | 40 mg |
| | Ethanol | 300 μl |
| | Water | 300 μl |
| | Dodecylazacycloheptan-2-one | 50 μl |
| | Propylene glycol | to 1 ml |

What is claimed is:

1. A pyrimidine compound of the Formula I

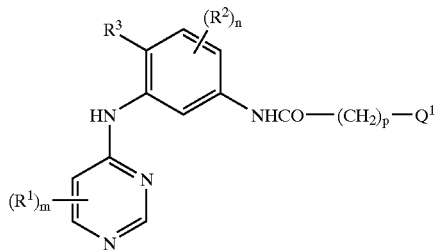

I wherein m is 0, 1, 2 or 3 and each R¹ group, which may be the same or different, is selected from hydroxy, halogeno, trifluoromethyl, cyano, mercapto, nitro, amino, carboxy, carbamoyl, formyl, sulphamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

Q²—X¹— wherein X¹ is a direct bond or is selected from O, S, SO, SO₂, N(R⁴), CO, CH(OR⁴), CON(R⁴), N(R⁴)CO, SO₂N(R⁴), N(R⁴)SO₂, OC(R⁴)₂, SC(R⁴)₂ and N(R⁴)C(R⁴)₂, wherein each R⁴ is hydrogen or (1–6C)alkyl, and Q² is aryl-(1–6C)alkyl, heteroaryl-(1–6C)alkyl, heterocyclyl or heterocyclyl-(1–6C)alkyl, or (R¹)ₘ is (1–3C)alkylenedioxy, and wherein a single pair of adjacent carbon atoms in a (2–6C)alkylene chain within a R¹ substituent is optionally separated by the insertion of a group selected from O, S, SO, SO₂, N(R⁵), CO, CH(OR⁵), CON(R⁵), N(R⁵)CO, SO₂N(R¹) and N(R⁵)SO₂ wherein R⁵ is hydrogen or (1–6C)alkyl, and wherein any aryl, heteroaryl or heterocyclyl group within a substituent on R¹ optionally bears 1, 2 or 3 substituents, which may be the same or different, selected from halogeno, trifluoromethyl, cyano, nitro, hydroxy, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X²—Q³ wherein X² is a direct bond or is selected from O and N(R⁷), wherein R⁷ is hydrogen or (1–6C)alkyl, and Q³ is aryl, aryl-(1–6C)alkyl, heteroaryl, heteroaryl-(1–6C)alkyl, heterocyclyl or heterocyclyl-(1–6C)alkyl, and any Q³ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl]amino, and wherein any heterocyclyl group within a substituent on R¹ optionally bears 1 or 2 oxo or thioxo substituents, and wherein any CH₂ or CH₃ group within a R¹ substituent optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino;

R³ is hydrogen, halogeno or (1–6C)alkyl;

n is 0, 1 or 2 and each R² group, which may be the same or different, is selected from hydroxy, halogeno, trifluoromethyl, cyano, mercapto, nitro, amino, carboxy, (1–6C)alkoxycarbonyl, (1–6C)alkyl, (1–6C)alkoxy, (1C)alkylamino and di-[(1–6C)alkyl]amino;

p is 0, 1, 2, 3 or 4; and

Q¹ is aryl or heteroaryl and Q¹ is optionally substituted with 1, 2 or 3 substituents, which may be the same or different, selected from hydroxy, halogeno, trifluoromethyl, cyano, mercapto, nitro, amino, carboxy, carbamoyl, formyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino or with a (1–3C)alkylenedioxy group, or from a group of the formula:

—X³—Q⁴ wherein X³ is a direct bond or is selected from O and N(R⁸), wherein R⁸ is hydrogen or (1–6C)alkyl, and Q⁴ is aryl, aryl-(1–6C)alkyl, heteroaryl, heteroaryl-(1–6C)alkyl, heterocyclyl or heterocyclyl-(1–6C)alkyl, and any Q⁴ group optionally bears 1 or 2 substituents, which may be the same or different, selected from halogeno, trifluoromethyl, cyano, hydroxy, amino, (1–6C)alkyl, (1–6C)alkoxy, (1–6C)alkylamino and di-[(1–6C)alkyl]amino, and wherein any heterocyclyl group within a substituent on Q¹ optionally bears 1 or 2 oxo or thioxo substituents, and wherein a single pair of adjacent carbon atoms in a (2–6C)alkylene chain within a Q¹ substituent is optionally separated by the insertion of a group selected from O, S, SO, SO$_2$, N(R$^9$), CO, CH(OR$^9$), CON(R$^9$), N(R$^9$)CO, SO$_2$N(R$^9$) and N(R$^9$)SO$_2$ wherein R$^9$ is hydrogen or (1–6C)alkyl, and wherein any CH$_2$ or CH$_3$ group within a Q$^1$ group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (16C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino;

or a pharmaceutically-acceptable salt or in-vivo-cleavable ester formed from an available carboxy group thereof.

2. A pyrimidine compound of the Formula I according to claim 1 wherein m is 0, 1, 2 or 3, and each R$^1$ group, which may be the same or different, is selected from hydroxy, fluoro, chloro, bromo, trifluoromethyl, amino, carbamoyl, methyl, ethyl, propyl, methoxy, ethoxy, propoxy, methylthio, methylsulphinyl, methylsulphonyl, methylamino, ethylamino, propylamino, isopropylamino, butylamino, allylamino, propargylamino, dimethylamino, diethylamino, dipropylamino, N-allyl-N-methylamino, N-methylcarbamoyl, N,N-dimethylcarbamoyl and acetamido, or from a group of the formula:

Q$^2$—X$^1$— wherein X$^1$ is a direct bond or is selected from O, NH and N(Me) and Q$^2$ is benzyl, 2-furylmethyl, 3-furylmethyl, 2-thienylmethyl, 3-thienylmethyl, 1-imidazolylmethyl, 2-imidazolylmethyl, 2-imidazol-1-ylethyl, 3-imidazol-1-ylpropyl, 4-imidazol-1-ylbutyl, 2-oxazolylmethyl, 4-oxazolylmethyl, 5-oxazolylmethyl, 2-thiazolylmethyl, 4-thiazolylmethyl, 5-thiazolylmethyl, 1,2,3-triazol-1-ylmethyl, 2-(1,2,3-triazol-1-yl)ethyl, 3-(1,2,3-triazol-1-yl)propyl, 1,2,4-triazol-1-ylmethyl, 2-(1,2,4-triazol-1-yl)ethyl, 3-(1,2,4-triazol-1-yl)propyl, 2-pyridylmethyl, 3-pyridylmethyl, 4-pyridylmethyl, 2-pyrid-2-ylethyl, 2-pyrid-3-ylethyl, 2-pyrid-4-ylethyl, 3-pyrid-2-ylpropyl, 3-pyrid-3-ylpropyl, 3-pyrid-4-ylpropyl, pyrrolidin-1-yl, pyrrolidin-2-yl, pyrrolidin-3-yl, morpholino, tetrahydro-4H-1,4-thiazin-4-yl, 1,1-dioxotetrahydro-4H-1,4-thiazin-4-yl, piperidino, piperidin-2-yl, piperidin-3-yl, piperidin-4-yl, homopiperidin-1-yl, homopiperidin-2-yl, homopiperidin-3-yl, homopiperidin-4-yl, piperazin-1-yl, homopiperazin-1-yl, pyrrolidin-1-ylmethyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, pyrrolidin-3-ylmethyl, 2-pyrrolidin-3-ylethyl, 3-pyrrolidin-3-ylpropyl, imidazolidin-1-ylmethyl, 2-imidazolidin-1-ylethyl, 3-imidazolidin-1-ylpropyl, imidazolidin-2-ylmethyl, 2-imidazolidin-2-ylethyl, 3-imidazolidin-2-ylpropyl, morpholinomethyl, 2-morpholinoethyl, 3-morpholinopropyl, morpholin-2-ylmethyl, 2-morpholin-2-ylethyl, 3-morpholin-2-ylpropyl, morpholin-3-ylmethyl, 2-morpholin-3-ylethyl, 3-morpholin-3-ylpropyl, tetrahydro-4H-1,4-thiazin-4-ylmethyl, 2-(tetrahydro-4H-1,4-thiazin-4-yl)ethyl, 3-(tetrahydro-4H-1,4-thiazin-4-yl)propyl, 1,1-dioxotetrahydro-4H-1,4-thiazin-4-ylmethyl, 2-(1,1-dioxotetrahydro-4H-1,4-thiazin-4-yl)ethyl, 3-(1,1-dioxotetrahydro-4H-1,4-thiazin-4-yl)propyl, piperidinomethyl, 2-piperidinoethyl, 3-piperidinopropyl, piperidin-2-ylmethyl, 2-piperidin-2-ylethyl, 3-piperidin-2-ylpropyl, piperidin-3-ylmethyl, 2-piperidin-3-ylethyl, 3-piperidin-3-ylpropyl, piperidin-4-ylmethyl, 2-piperidin-4-ylethyl, 3-piperidin-4-ylpropyl, homopiperidin-1-ylmethyl, 2-homopiperidin-1-ylethyl, 3-homopiperidin-1-ylpropyl, homopiperidin-2-ylmethyl, 2-homopiperidin-2-ylethyl, 3-homopiperidin-2-ylpropyl, homopiperidin-3-ylmethyl, 2-homopiperidin-3-ylethyl, 3-homopiperidin-3-ylpropyl, homopiperidin-4-ylmethyl, 2-homopiperidin-4-ylethyl, 3-homopiperidin-4-ylpropyl, piperazin-1-ylmethyl, 2-piperazin-1-ylethyl, 3-piperazin-1-ylpropyl, piperazin-2-ylmethyl, 2-piperazin-2-ylethyl, 3-piperazin-2-ylpropyl, homopiperazin-1-ylmethyl, 2-homopiperazin-1-ylethyl, 3-homopiperazin-1-ylpropyl, homopiperazin-2-ylmethyl, 2-homopiperazin-2-ylethyl or 3-homopiperazin-2-ylpropyl, and wherein a single pair of adjacent carbon atoms in a (2–6C)alkylene chain within a R$^1$ substituent is optionally separated by the insertion of a group selected from O and NH, and wherein any aryl, heteroaryl or heterocyclyl group within a substituent on R$^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy propoxy, isopropoxy, methoxycarbonyl, ethoxycarbonyl and tert-butoxycarbonyl, and wherein any heterocyclyl group within a substituent on R$^1$ optionally bears 1 or 2 oxo substituents, and wherein any CH$_2$ or CH$_3$ group within a R$^1$ substituent optionally bears on each said CH$_2$ or CH$_3$ group 1 or 2 methyl substituents or a substituent selected from hydroxy, amino, methoxy, ethoxy, methylsulphonyl, methylamino, ethylamino, dimethylamino and diethylamino;

each of n and p is 0;

R$^3$ is hydrogen or methyl; and

Q$^1$ is phenyl, 2-furyl, 2-thienyl, 4-oxazolyl, 5-isoxazolyl, 2- or 4-imidazolyl, 3- or 4-pyrazolyl, 4-thiazolyl, 5-isothiazolyl, 2-, 3- or 4-pyridyl, 4-pyridazinyl, 4- or 5-pyrimidinyl, 2- or 6-benzofuranyl, 2- or 6-indolyl, 2- or 6-benzothiophenyl, 2- or 6-quinolyl or 2- or 4-dibenzofuranyl which optionally bears 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonylamino, 1-azetidinyl, 3-pyrrolin-1-yl, 1-pyrrolidinyl, morpholino, tetrahydro-4H-1,4-thiazin-4-yl, 1,1-dioxotetrahydro-4H-1,4-thiazin-4-yl, 1-piperidinyl, 1-homopiperidinyl, 1-piperazinyl and 1-homopiperazinyl, or from a group of the formula:

—$X^3$—$Q^4$ wherein $X^3$ is a direct bond or is selected from O, NH and N(Me) and $Q^4$ is phenyl, 2- or 3-furyl, 2- or 3-thienyl, 1- or 2-imidazolyl, 2-, 4- or 5-oxazolyl, 2-, 4- or 5-thiazolyl, 2-, 3- or 4-pyridyl, 3- or 4-pyridazinyl, 2- or 4-pyrimidinyl or 2-pyrazinyl, and any $Q^4$ group optionally bears 1 or 2 substituents, which may be the same or different, selected from fluoro, chloro, bromo, trifluoromethyl, hydroxy, amino, methyl, ethyl, methoxy, ethoxy, methylamino, ethylamino, dimethylamino and diethylamino, and wherein any heterocyclyl group within $Q^1$ optionally bears 1 or 2 oxo substituents, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester formed from an available carboxy group thereof.

3. A pyrimidine compound of the Formula I according to claim 1 wherein m is 0, 1 or 2 and each $R^1$ group, which may be the sane or different, is selected from hydroxy, fluoro, chloro, bromo, trifluoromethyl, amino, carbamoyl, methyl, ethyl, propyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, N-methylcarbamoyl, N,N-dimethylcarbamoyl, acetamido, benzyloxy, benzylamino, N-benzyl-N-methylamino, 2-furylmethoxy, 3-furylmethoxy, 2-imidazol-1-ylethylamino, 3-imidazol-1-ylpropylamino, 2-(1,2,4-triazol-1-yl)ethylamino, 3-(1,2,4-triazol-1-yl) propylamino, 2-pyridylmethoxy, 3-pyridylmethoxy, 4-pyridylmethoxy, pyrrolidin-1-yl, pyrrolidin-3-yloxy, pyrrolidin-3-ylamino, N-methyl-N-(3-pyrrolidinyl) amino, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl) amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethoxy, 3-imidazolidin-1-ylpropoxy, imidazolidin-2-ylmethoxy, 2-imidazolidin-2-ylethoxy, 3-imidazolidin-2-ylpropoxy, 2-imidazolidin-1-ylethylamino, 3-imidazolidin-1-ylpropylamino, 2-imidazolidin-2-ylethylamino, 3-imidazolidin-2-ylpropylamino, 2-morpholinoethoxy, 3-morpholinopropoxy, 2-morpholinoethylamino, 3-morpholinopropylamino, morpholin-2-ylmethoxy, 2-morpholin-2-ylethoxy, 3-morpholin-2-ylpropoxy, 2-morpholin-2-ylethylamino, 3-morpholin-2-ylpropylamino, morpholin-3-ylmethoxy, 2-morpholin-3-ylethoxy, 3-morpholin-3-ylpropoxy, 2-morpholin-3-ylethylamino, 3-morpholin-3-ylpropylamino, 2-piperidinoethoxy, 3-piperidinopropoxy, 2-piperidinoethylamino, 3-piperidinopropylamino, piperidin-2-ylmethoxy, 2-piperidin-2-ylethoxy, 3-piperidin-2-ylpropoxy, piperidin-2-ylmethylamino, 2-piperidin-2-ylethylamino, 3-piperidin-2-ylpropylamino, piperidin-3-ylmethoxy, 2-piperidin-3-ylethoxy, 3-piperidin-3-ylpropoxy, piperidin-3-ylmethylamino, 2-piperidin-3-ylethylamino, 3-piperidin-3-ylpropylamino, piperidin-4-ylmethoxy, 2-piperidin-4-ylethoxy, 3-piperidin-4-ylpropoxy, piperidin-4-ylmethylamino, 2-piperidin-4-ylethylamino, 3-piperidin-4-ylpropylamino, 2-homopiperidin-1-ylethoxy, 3-homopiperidin-1-ylpropoxy, 2-homopiperidin-1-ylethylamino, 3-homopiperidin-1-ylpropylamino, homopiperidin-2-ylmethoxy, homopiperidin-2-ylmethylamino, homopiperidin-3-ylmethoxy, homopiperidin-3-ylmethylamino, homopiperidin-4-ylmethoxy, homopiperidin-4-ylmethylamino, 2-piperazin-1-ylethoxy, 3-piperazin-1-ylpropoxy, 2-piperazin-1-ylethylamino, 3-piperazin-1-ylpropylamino, piperazin-2-ylmethoxy, piperazin-2-ylmethylamino, 2-piperazin-2-ylethoxy, 3-piperazin-2-ylpropoxy, 2-piperazin-2-ylethylamino, 3-piperazin-2-ylpropylamino, 2-homopiperazin-1-ylethoxy, 3-homopiperazin-1-ylpropoxy, 2-homopiperazin-1-ylethylamino, 3-homopiperazin-1-ylpropylamino, homopiperazin-2-ylmethoxy or homopiperazin-2-ylmethylamino, and wherein any aryl, heteroaryl or heterocyclyl group within a substituent on $R^1$ optionally bears 1, 2 or 3 substituents, which may be the same or different, selected from hydroxy, fluoro, chloro, trifluoromethyl, amino, methyl, ethyl, propyl, isopropyl, methoxy, ethoxy propoxy, isopropoxy, methoxycarbonyl, ethoxycarbonyl and tert-butoxycarbonyl, and wherein any heterocyclyl group within a substituent on $R^1$ optionally bears 1 or 2 oxo substituents, and wherein any $CH_2$ or $CH_3$ group within a $R^1$ substituent optionally bears on each said $CH_2$ or $CH_3$ group 1 or 2 methyl substituents or a substituent selected from hydroxy, amino, methoxy, ethoxy, methylsulphonyl, methylamino, ethylamino, dimethylamino and diethylamino;

each of n and p is 0;

$R^3$ is methyl; and $Q^1$ is phenyl or 3- or 4-pyridyl which optionally bears 1, 2 or 3 substituents, which may be the same or different, selected from hydroxy, fluoro, chloro, bromo, trifluoromethyl, cyano, amino, methyl, ethyl, propyl, methoxy, ethoxy, propoxy, methylamino, ethylamino, propylamino, isopropylamino, dimethylamino, diethylamino, dipropylamino, N-ethyl-N-methylamino, N-methyl-N-propylamino, acetamido, N-methylacetamido, methanesulphonylamino, ethanesulphonylamino, N-methylmethanesulphonyl-amino, 1-azetidinyl, 3-pyrrolin-1-yl, 1-pyrrolidinyl, morpholino, 1-piperidinyl, 1-homopiperidinyl, 1-piperazinyl and 1-homopiperazinyl, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester formed from an available carboxy group thereof.

4. A pyrimidine compound of the Formula I according to claim 1 wherein m is 0, 1 or 2 and each $R^1$ group, which may be the same or different, is selected from fluoro, chloro, bromo, amino, carbamoyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, pyrrolidin-3-yloxy, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethylamino, 3-imidazolidin-1-ylpropylamino, 2-morpholinoethoxy, 3-morpholinopropoxy, 2-morpholinoethylamino, 3-morpholinopropylamino, 2-piperidinoethoxy, 3-piperidinopropoxy, 2-piperidinoethylamino, 3-piperidinopropylamino, piperidin-3-ylmethoxy, piperidin-4-ylmethoxy, 2-piperazin-1-ylethoxy, 3-piperazin-1-ylpropoxy, 2-piperazin-1-ylethylamino, 3-piperazin-1-ylpropylamino or piperazin-2-ylmethoxy, and wherein any heterocyclyl group within a substituent on $R^1$ optionally bears 1 or 2 substituents, which may be the same or different, selected from hydroxy, fluoro, chloro, methyl, ethyl, propyl, isopropyl, methoxy, ethoxy, methoxycarbonyl, ethoxycarbonyl and tert-butoxycarbonyl, and wherein any heterocyclyl group within a substituent on $R^1$ optionally bears an oxo substituent, and wherein any $CH_2$ or $CH_3$ group within a $R^1$ substituent optionally bears on each said $CH_2$ or $CH_3$ group 1 or 2 methyl substituents or a substituent selected from hydroxy, amino, methylamino, ethylamino, dimethylamino and diethylamino;

each of n and p is 0;

$R^3$ is methyl; and $Q^1$ is phenyl or 4-pyridyl which optionally bears 1, 2 or 3 substituents, which may be the same or different, selected from fluoro, chloro, trifluoromethyl, amino, methyl, methoxy, methylamino, ethylamino, dimethylamino, diethylamino, 1-pyrrolidinyl, morpholino, piperidino, 1-homopiperidinyl, 1-piperazinyl and 1-homopiperazinyl, and wherein any $CH_2$ or $CH_3$ group within a $Q^1$ group optionally bears on each said $CH_2$ or $CH_3$ group 1 or 2 methyl substituents or a substituent selected from hydroxy, amino, methoxy, ethoxy, methylamino, ethylamino, dimethylamino and diethylamino;

or a pharmaceutically acceptable salt or in-vivo-cleavable ester formed from an available carboxy group thereof.

5. A pyrimidine compound of the Formula I according to claim 1 wherein m is 1 or 2 and each $R^1$ group, which may be the same or different, is selected from chloro, carbamoyl, 3-dimethylaminopropoxy, 3-dimethylamino-2,2-dimethylpropoxy, methylthio, 3-diethylaminopropylamino, 3-dimethylamino-2,2-dimethylpropylamino, 3-dimethylamino-2-hydroxypropylamino, N-isopropylpyrrolidin-3-yloxy, piperidin-4-yloxy, N-methylpiperidin-4-yloxy, N-ethylpiperidin-3-ylamino, N-methylpiperidin-4-ylamino, N-methyl-N-(N-methylpiperidin-4-yl)amino, 3-pyrrolidin-1-ylpropylamino, N-methylpyrrolidin-2-ylmethoxy, 2-(N-methylpyrrolidin-2-yl)ethoxy, 2-(N-methylpyrrolidin-2-yl)ethylamino, N-methylpiperidin-3-ylmethoxy and N,N'-dimethylpiperazin-2-ylmethoxy;

each of n and p is 0;

$R^3$ is methyl; and $Q^1$ is phenyl which bears 1 or 2 substituents, which may be the same or different, selected from fluoro, trifluoromethyl, dimethylamino, 1-pyrrolidinyl, morpholino, piperidino, 1-homopiperidinyl, 1-piperazinyl and 1-homopiperazinyl, or $Q^1$ is 4-pyridyl which bears 1 substituent selected from dimethylamino, 1-pyrrolidinyl, morpholino, piperidino, 1-homopiperidinyl, 1-piperazinyl and 1-homopiperazinyl, or a pharmaceutically acceptable salt or in-vivo-cleavable ester formed from an available carboxy group thereof.

6. A pyrimidine compound of the Formula I according to claim 1 wherein m is 0, 1 or 2 and each $R^1$ group, which may be the same or different, is selected from fluoro, chloro, bromo, amino, carbamoyl, methoxy, ethoxy, propoxy, methylthio, methylamino, ethylamino, propylamino, isopropylamino, butylamino, allylamino, dimethylamino, diethylamino, dipropylamino, N-allyl-N-methylamino, pyrrolidin-3-yloxy, morpholino, tetrahydro-4H-1,4-thiazin-4-yl, piperidino, piperidin-3-yloxy, piperidin-4-yloxy, piperidin-3-ylamino, piperidin-4-ylamino, N-methyl-N-(3-piperidinyl)amino, N-methyl-N-(4-piperidinyl)amino, homopiperidin-1-yl, homopiperidin-3-yloxy, homopiperidin-4-yloxy, piperazin-1-yl, homopiperazin-1-yl, 2-pyrrolidin-1-ylethoxy, 3-pyrrolidin-1-ylpropoxy, 2-pyrrolidin-1-ylethylamino, 3-pyrrolidin-1-ylpropylamino, pyrrolidin-2-ylmethoxy, 2-pyrrolidin-2-ylethoxy, 3-pyrrolidin-2-ylpropoxy, pyrrolidin-2-ylmethylamino, 2-pyrrolidin-2-ylethylamino, 3-pyrrolidin-2-ylpropylamino, pyrrolidin-3-ylmethoxy, 2-pyrrolidin-3-ylethoxy, 3-pyrrolidin-3-ylpropoxy, pyrrolidin-3-ylmethylamino, 2-pyrrolidin-3-ylethylamino, 3-pyrrolidin-3-ylpropylamino, 2-imidazolidin-1-ylethylamino, 3-imidazolidin-1- ylpropylamino, 2-morpholinoethoxy, 3-morpholinopropoxy, 2-morpholinoethylamino, 3-morpholinopropylamino, 2-piperidinoethoxy, 3-piperidinopropoxy, 2-piperidinoethylamino, 3-piperidinopropylamino, piperidin-3-ylmethoxy, piperidin-4-ylmethoxy, 2-piperazin-1-ylethoxy, 3-piperazin-1-ylpropoxy, 2-piperazin-1-ylethylamino, 3-piperazin-1-ylpropylamino or piperazin-2-ylmethoxy, and wherein any heterocyclyl group within a substituent on $R^1$ optionally bears 1 or 2 substituents, which may be the same or different, selected from hydroxy, fluoro, chloro, methyl, ethyl, propyl, isopropyl, methoxy, ethoxy, methoxycarbonyl, ethoxycarbonyl and tert-butoxycarbonyl, and wherein any heterocyclyl group within a substituent on $R^1$ optionally bears an oxo substituent, and wherein any $CH_2$ or $CH_3$ group within a $R^1$ substituent optionally bears on each said $CH_2$ or $CH_3$ group 1 or 2 methyl substituents or a substituent selected from hydroxy, amino, methylamino, ethylamino, dimethylamino and diethylamino;

each of n and p is 0;

$R^3$ is methyl; and $Q^1$ is 4-dibenzofuranyl which optionally bears 1 or 2 substituents, which may be the same or different, selected from fluoro, chloro, trifluoromethyl, amino, methyl, methoxy, methylamino, ethylamino, dimethylamino and diethylamino;

or a pharmaceutically acceptable salt or in-vivo-cleavable ester formed from an available carboxy group thereof.

7. A pyrimidine compound of the Formula I according to claim 1 wherein m is 1 and the $R^1$ group is selected from chloro, carbamoyl, methoxy, ethoxy, 3-dimethylaminopropoxy, 3-dimethylamino-2,2-dimethylpropoxy, methylthio, N-isopropylpyrrolidin-3-yloxy, piperidin-4-yloxy, N-methylpiperidin-4-yloxy, N-ethylpiperidin-4-yloxy, N-propylpiperidin-4-yloxy, N-methylpyrrolidin-2-ylmethoxy, 2-(N-methylpyrrolidin-2-yl)ethoxy, N-methylpiperidin-3-ylmethoxy and N,N'-dimethylpiperazin-2-ylmethoxy;

each of n and p is 0;

$R^3$ is methyl; and $Q^1$ is 4-dibenzofuranyl which optionally bears 1 or 2 substituents, which may be the same or different, selected from fluoro, chloro, trifluoromethyl and dimethylamino, or a pharmaceutically acceptable salt or in-vivo-cleavable ester formed from an available carboxy group thereof.

8. A pyrimidine compound of the Formula I according to claim 1 selected from:—

6-carbamoyl-2-chloro-4-[5-(3-fluoro-5-morpholinobenzamido)-2-methylanilino]pyrimidine, 4-[5-(3-fluoro-5-morpholinobenzamido)-2-methylanilino]-2-methylthiopyrimidine, 2-chloro-4-[2-methyl-5-(2-morpholinopyrid-4-ylcarbonylamino)anilino]pyrimidine, 4-[2-methyl-5-(2-morpholino- pyrid-4-ylcarbonylamino)anilino]-2-(N-methylpiperidin-4-yloxy)pyrimidine, 2-(3-dimethylaminopropoxy)-4-[2-methyl-5-(2-morpholinopyrid-4-ylcarbonylamino) anilino]pyrimidine, 2-(3-dimethylamino-2,2-dimethylpro- poxy)-4-[2-methyl-5-(2-morpholinopyrid-4-ylcarbonylamino)anilino] pyrimidine, 4-[2-methyl-5-(2-morpholinopyrid-4-ylcarbonylamino)anilino]-2-(N-methylpiperidin-3-ylmethoxy)pyrimidine, 2-[N-methyl-N-(N-methylpiperidin-4-yl)amino]-4-[2-methyl-5-(2-morpholinopyrid-4-ylcarbonylamino)anilino] pyrimidine, 4-[2-methyl-5-(2-morpholino- pyrid-4-ylcarbonylamino)anilino]-2-[2-(N-methylpyrrolidin-2-yl)ethylamino]pyrimidine, 2-(3-dimethylamino-2,2-dimethylpropoxy)-4-[5-(3-fluoro-5-morpholinobenzamido)-2-methylanilino]pyrimidine, 4-[5-(3-fluoro-5-morpholinobenzamido)-2-methylanilino]-2-(N-methylpiperidin-4-yloxy) pyrimidine, 4-[5-(3-fluoro-5-morpholinobenzamido)-2-methylanilino]-2-(N-propylpiperidin-4-yloxy) pyrimidine, 4-[5-(4-dibenzofuranylcarbonylamino)-2-methylanilino]-2-(N-methylpiperidin-4-yloxy) pyrimidine and 4-[5-(4-dibenzofuranylcarbonylamino)-2-methylanilino]-2-(3-dimethylamino-2,2-dimethylpropoxy)pyrimidine;

or a pharmaceutically acceptable salt or in-vivo-cleavable ester formed from an available carboxy group thereof.

9. A process for preparing a pyrimidine compound of the Formula I, or a pharmaceutically-acceptable salt or in-vivo-cleavable ester formed from an available carboxy group thereof, according to claim 1:—

(a) reacting an aniline of the Formula II

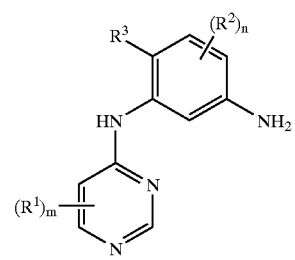

II with an acid of the Formula III, or a reactive derivative thereof,

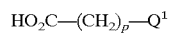

III under standard amide bond forming conditions, wherein variable groups are as defined in claim 1 and wherein any functional groups are protected if necessary;

(b) the reaction of an activated heteroaryl compound of the Formula V

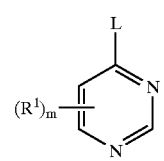

V wherein L is a displaceable group, with an aniline of the Formula VII

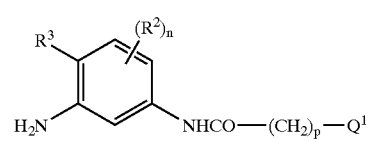

VII wherein variable groups are as defined in claim 1 and wherein any functional group is protected if necessary;

(c) for a compound of the Formula I, or a pharmaceutically-acceptable salt or in-vivo-cleavable ester thereof, wherein R¹ or a substituent on Q¹ is an amino, (1–6C)alkylamino, di-[(1–6C)alkyl]amino, substituted (1–6C)alkylamino, substituted di-[(1–6C)alkyl]amino, a N-linked heterocyclyl substituent or a heterocyclylamino substituent, the reaction of an appropriate amine with a pyrimidine compound of the Formula I wherein R¹ or a substituent on Q¹ as appropriate is a suitable displaceable group and wherein other variable groups are as defined in claim 1 and wherein any functional group is protected if necessary;

(d) for a compound of the Formula I, or a pharmaceutically-acceptable salt or in-vivo-cleavable ester thereof, wherein R¹ or a substituent on Q¹ is a (1–6C)alkoxy or substituted (1–6C)alkoxy substituent or a heterocyclyloxy substituent, the reaction of an appropriate alcohol with a pyrimidine compound of the Formula I wherein R¹ or a substituent on Q¹ as appropriate is a suitable displaceable group and wherein other variable groups are as defined in claim 1 and wherein any functional group is protected if necessary;

(e) for a compound of the Formula I, or a pharmaceutically-acceptable salt or in-vivo-cleavable ester thereof, wherein m is 0, the cleavage of a compound of the Formula I, wherein m is 1, 2 or 3 and each R¹ substituent is a halogeno group and wherein other variable groups are as defined in claim 1 and wherein any functional group is protected if necessary;

(f) for a compound of the Formula I, or a pharmaceutically-acceptable salt or in-vivo-cleavable ester thereof, wherein R¹ or Q¹ contains a (1–6C)alkoxy or substituted (1–6C)alkoxy group or a (1–6C)alkylamino or substituted (1–6C)alkylamino group, the alkylation of a pyrimidine compound of the Formula I wherein R¹ or Q¹ contains a hydroxy group or a primary or secondary amino group as appropriate, and wherein other variable groups are as defined in claim 1 and wherein any functional group is protected if necessary;

(g) for a compound of the Formula I, or a pharmaceutically-acceptable salt or in-vivo-cleavable ester thereof, wherein R¹ is a hydroxy group, the cleavage of a compound of the Formula I, wherein R¹ is a halogeno group and wherein other variable groups are as defined in claim 1 and wherein any functional group is protected if necessary; or (h) for a compound of the Formula I, or a pharmaceutically-acceptable salt or in-vivo-cleavable ester thereof, wherein R¹ is a (1–6C)alkylsulphinyl or (1–6C)alkylsulphonyl group, the oxidation of a compound of the Formula I, wherein R¹ is a (1–6C)alkylthio group and wherein other variable groups are as defined in claim 1 and wherein any functional group is protected if necessary, and thereafter (i) removing any protecting groups; and
(ii) optionally forming a pharmaceutically-acceptable salt or in-vivo-cleavable ester.

10. A pharmaceutical composition which comprises a pyrimidine compound of the Formula I, or a pharmaceutically-acceptable or in-vivo-cleavable ester formed from an available carboxy group thereof, as defined in claim 1 in association with a pharmaceutically-acceptable diluent or carrier.

11. A method for inhibiting the production of TNFα in a warm-blooded animal in need thereof comprising administering to said animal a TNFα production inhibiting amount of a pyrimidine compound of the Formula I, or a pharmaceutically-acceptable salt or in-vivo-cleavable ester formed from an available carboxy group thereof, as defined in claim 1.

12. A method for the treatment of rheumatoid arthritis in a warm-blooded animal in need thereof comprising administering to said animal an effective amount of a pyrimidine compound of the Formula I, or a pharmaceutically-acceptable salt or in-vivo-cleavable ester formed from an available carboxy group thereof, as defined in claim 1.

* * * * *